US009157096B2

(12) United States Patent
Kawaoka et al.

(10) Patent No.: US 9,157,096 B2
(45) Date of Patent: *Oct. 13, 2015

(54) REASSORTANT INFLUENZA VIRUSES FOR VACCINES

(71) Applicant: Wisconsin Alumni Research Foundation, Madison, WI (US)

(72) Inventors: Yoshihiro Kawaoka, Middleton, WI (US); Gabriele Neumann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,915

(22) Filed: Jan. 17, 2014

(65) Prior Publication Data

US 2014/0206062 A1 Jul. 24, 2014

Related U.S. Application Data

(63) Continuation of application No. 12/718,573, filed on Mar. 5, 2010, now abandoned, which is a continuation of application No. 09/971,372, filed on Oct. 4, 2001, now Pat. No. 8,715,940, which is a continuation of application No. PCT/US00/09021, filed on Apr. 5, 2000.

(60) Provisional application No. 60/127,912, filed on Apr. 6, 1999, provisional application No. 60/132,839, filed on May 6, 1999.

(51) Int. Cl.
| | |
|---|---|
| *G01N 33/53* | (2006.01) |
| *C12N 9/22* | (2006.01) |
| *C12N 7/02* | (2006.01) |
| *C12N 15/85* | (2006.01) |
| *A61K 39/145* | (2006.01) |
| *C07K 14/005* | (2006.01) |
| *C12N 7/00* | (2006.01) |
| *C12N 15/86* | (2006.01) |
| *A61K 39/12* | (2006.01) |
| *A61K 39/00* | (2006.01) |
| *A61K 48/00* | (2006.01) |

(52) U.S. Cl.
CPC ........... *C12N 15/85* (2013.01); *A61K 39/12* (2013.01); *A61K 39/145* (2013.01); *A61K 48/0091* (2013.01); *C07K 14/005* (2013.01); *C12N 7/00* (2013.01); *C12N 15/86* (2013.01); *A61K 39/00* (2013.01); *A61K 48/00* (2013.01); *A61K 2039/525* (2013.01); *A61K 2039/5258* (2013.01); *C12N 2760/16122* (2013.01); *C12N 2760/16123* (2013.01); *C12N 2760/16134* (2013.01); *C12N 2760/16143* (2013.01); *C12N 2760/16151* (2013.01); *C12N 2800/30* (2013.01); *C12N 2810/6081* (2013.01)

(58) Field of Classification Search
USPC ........................................ 435/7.1, 199.1, 239
See application file for complete search history.

(56) References Cited

U.S. PATENT DOCUMENTS

| | | | |
|---|---|---|---|
| 4,071,618 A | 1/1978 | Konobe et al. |
| 4,659,569 A | 4/1987 | Mitsuhashi et al. |
| 5,166,057 A | 11/1992 | Palese et al. |
| 5,596,079 A | 1/1997 | Smith et al. |
| 5,716,821 A | 2/1998 | Wertz et al. |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,976,807 A | 11/1999 | Horlick et al. |
| 5,994,526 A | 11/1999 | Gossele et al. |
| 6,033,886 A | 3/2000 | Conzelmann |
| 6,146,642 A | 11/2000 | Garcia-Sastre et al. |
| 6,312,064 B1 | 11/2001 | Kokie |
| 6,322,967 B1 | 11/2001 | Parkin |
| 6,544,785 B1 | 4/2003 | Palese |
| 6,649,372 B1 | 11/2003 | Palese |
| 6,830,892 B2 | 12/2004 | Marasco et al. |
| 6,887,699 B1 | 5/2005 | Palese et al. |
| 6,951,754 B2 | 10/2005 | Hoffman |
| 7,384,744 B2 | 6/2008 | Enenkel |
| 2003/0035814 A1 | 2/2003 | Kawaoka et al. |
| 2006/0057116 A1 | 3/2006 | Kawaoka et al. |
| 2006/0134138 A1 | 6/2006 | Kawaoka et al. |

FOREIGN PATENT DOCUMENTS

| | | |
|---|---|---|
| CA | 2423891 A1 | 12/1966 |
| CA | 2164946 A1 | 12/1995 |
| EP | 0 702 085 | 3/1996 |
| EP | 1 185 615 | 3/2002 |
| EP | 1 820 853 | 8/2007 |
| WO | 96/10632 | 4/1996 |
| WO | 96/10633 | 4/1996 |
| WO | 96/10641 | 4/1996 |
| WO | 96/40955 | 12/1996 |
| WO | 97/14434 A1 | 4/1997 |

(Continued)

OTHER PUBLICATIONS

Neumann et al, "Synthesis of Influenza Virus:New Impetus from an Old Enzyme, RNA Polymerase I," (Jan. 2000)Virus Research 82(1-2):153-158.

(Continued)

*Primary Examiner* — Michael Wilson
(74) *Attorney, Agent, or Firm* — McDonnell Boehnen Hulbert & Berghoff LLP

(57) ABSTRACT

The invention provides compositions and methods useful to prepare segmented, negative strand RNA viruses, e.g., orthomyxoviruses such as influenza A viruses, entirely from cloned cDNAs and in the absence of helper virus.

11 Claims, 15 Drawing Sheets

(56) References Cited

FOREIGN PATENT DOCUMENTS

| WO | 98/02530 | 1/1998 |
|---|---|---|
| WO | 98/10086 | 3/1998 |
| WO | 98/53078 | 11/1998 |
| WO | 00/53786 | 9/2000 |
| WO | 00/60050 | 10/2000 |
| WO | 2004/112831 | 12/2004 |
| WO | 2005/028658 | 3/2005 |

OTHER PUBLICATIONS

Neumann et al, "Generation of Influenza A virus from Cloned cDNAs-Historical Perspective and Outlook for the New Millenium," Rev. Med. Virol. 12(1):13-30.
Fortes, et al, "Influenza virus NS1 protein inhibits pre-mRNA splicing and blocks mRNA nucleocytoplasmic transport," The EMBO Journal, 13:704-712 (1994).
Banerjee et al, "Gene Expression of Vesicular Stomatitis Virus Genome RNA," Virology 188:417-428 (1992).
Baron et al, "Rescue of Rinderpest Virus from Cloned cDNA," Journal of Virology 71:1265-1271 (1997).
Beare et al, "Trials in Man with Live Recombinants made From A/PR/8/34 (H0 N1) and Wild H3 N2 Influenza Viruses," The Lancet, Oct. 18, 1975, pp. 729-732.
Boyer et al, "Infectious Transcripts and cDNA Clones of NA Viruses," Virology, 198:415-426 (1994).
Bridgen et al, Rescue of a segmented negative-strand RNA virus entirely from clones complementary DNAs,: Proc. Natl. Acad. Sci. USA 93:15400-15404 (1996).
Buchholz et al, "Generation of Bovine Respiratory Syncytial Virus (BRSV) from cDNA:BRSV NS2 is not Essential for Virus Replication in Tissue Culture, . . . ," Journal of Virology 73:251-259 (1999).
Bukreyev et al, "Recovery of Infectious Respiratory Syncytial Virus Expressing an Additional, Foreign Gene," Journal of Virology 70:6634-6641 (1996).
Castrucci et al, "Reverse Genetics System for Generation of an Influenza A Virus Mutant Containing a Deletion of the Carboxy-Terminal Residue of M2 Protein," Journal of Virology 69:2725-2728 (1995).
Chen et al, "Influenza A virus NS1 protein targets poly(A)-binding protein II of the cellular 3'-end processing machinery," The EMBO Journal, 18:2273-2283 (1999).
Clarke et al, "Rescue of Mumps Virus from cDNA," Journal of Virology, 74:4831-4838 (2000).
Collins et al, "Parainfluenza Viruses," Fields Virology, 41:1205-1241 (1996).
Collins et al, "Production of infectious human respiratory syncytial virus from clones cDNA confirms an essential role for the transcription elongation factor from the 5' proximal open reading frame of the M2 mRNA in gene expression . . . ," Proc. Natl. Acad. Sci. USA, 92:11563-11567.
Collins et al, "Rescue of synthetic analogs of respiratory syncytial virus genomic RNA and effect of truncations and mutations on the expression of a foreign reporter gene," Proc. Natl. Acad. Sci. USA, 88:9663-9667 (1991).
Conzelmann et al, Genetic Engineering of Animal RNA Viruses, Trends in Microbiology, 4:386-393 (1996).
Conzelmann et al, "Rescue of Synthetic Genomic RNA Analogs of Rabies Virus by Plasmid-Encoded Proteins," Journal of Virology, 68:713-719 (1994).
Conzelmann, "Genetic Manipulation of Non-segmented Negative-strand RNA Viruses," Journal of General Virology, 77:381-389 (1996).
Conzelmann, "Nonsegmented Negative-Strand RNA Viruses: Genetics and Manipulation of Viral Genomes," Annu. Rev. Genet., 32:123-162 (1998).
De et al, "Requirements and Functions of Vesicular Stomatitis virus L and NS Proteins in the Transcription Process in Vitro," Biochemical and Biophysical Research Communications, 126:40-49 (1985).
De et al, "Rescue of Synthetic Analogs of Genome RNA of Human Parainfluenza virus Type 3," Virology, 196:344-348 (1993).

De et al, "Reverse genetics of negative strand RNA viruses," Indian Journal of Biochemistry & Biophysics, 31:367-376 (1994).
De La Luna et al, "Influenza virus naked RNA can be expressed upon transfection into cells co-expressing the three subunits of the polymerase and the nucleoprotein from simian virus 40 recombinant viruses," Journal of General Virology, 74:535-539 (1993).
De La Luna et al, "Influenza Virus NS1 Protein Enhances the Rate of Translation Initiation of Viral mRNAs," Journal of Virology, 69:2427-2433 (1995).
Dimock et al, "Rescue of Synthetic Analogs of Genomic RNA and Replicative-Intermediate RNA of Human Parainfluenza Virus Type 3," Journal of Virology, 67:2772-2778 (1993).
Dreher et al, "Mutational Analysis of the Sequence and Structural Requirements in Brome Mosaic virus RNA for Minus Strand Promoter Activity," J. Mol. Biol., 201:31-40 (1988).
Dunn et al, "Transcription of a Recombinant Bunyavirus RNA Template by Transiently Expressed Bunyavirus Proteins," Virology, 211:133-143 (1995).
Durbin et al, "Recovery of Infectious Human Parainfluenza Virus Type 3 from cDNA," Virology, 235:323-332 (1997).
Elliott et al, "Rescue of Infectious Bunyavirus Entirely From Cloned cDNA," Abstract #96 10.Sup.Th International Conference on Negative Strand Viruses (1997).
Elliott et al, "Some highlights of virus research in 1990," Journal of General Virology, 72:1761-1779 (1991).
Emerson et al, "Both NS and L Proteins Are Required for In Vitro RNA Synthesis by Vesicular Stomatitis Virus," Journal of Virology, 15:1348-1356 (1975).
Enami et al, "An Influenza Virus Containing Nine Different RNA Segments," Virology, 185:291-298 (1991).
Enami et al, "High-Efficiency Formation of Influenza Virus Transfectants," Journal Virology, 65:2711-2713 (1991).
Enami et al, "Introduction of site-specific mutations into the genome of influenza virus," Proc. Natl. Acad. Sci. USA, 87:3802-3805 (1990).
Fahey et al, "Status of immune-based therapies in HIV infection and AIDS," Clin. Exp. Immunol., 88:1-5 (1992).
Fodor et al, "Rescue of Influenza A Virus from Recombinant DNA," Journal of Virology, 73:9679-9682 (1999).
Garcia-Sastre, et al., "Genetic Manipulation of negative-Strand RNA Virus Genomes," Annu. Rev. Microbiol. 47:765-790 (1993).
Garcin, et al., "A highly recombinogenic system for the recovery of infectious Sendai paramyxovirus from cDNA: generation of a novel copy-back non defective interfering virus," The EMBO Journal 14:6087-6094 (1995).
Goto, et al., "Mutations Affecting the Sensitivity of the Influenza Virus Neuramnidase to 4-Guanidino-2,4-dideoxy-2,3-dehydro-N-acetylneuraminic Acid," Virology 238:265-272 (1997).
Grosfend, et al., "RNA Replication by Respiratory Syncytial Virus (RSV) is Directed by the N,P., and L Proteins: Transcription Also Occurs under These Conditions but requires RSV Superinfection for Efficient Synthesis . . . ," Journal of Virology 69:5677-5686 (1955).
Hatada, et al., "Binding of influenza A virus NA1 protein to dsRNA in vitro," Journal of General Virology 73:3325-3329(1992).
He, et al., "Recover of Infectious SV5 from Cloned DNA and Expression of a Foreign Gene," Virology 237:249-260 (1997).
Hoffman, et al., "An Infectious Clone of Human Parainfluenza virus type 3," Journal of Virology 71:4272-4277 (1997).
Huang, et al., "Determinaton of Influenza Virus proteins required for Genome Replication", Journal of Virology 64:5669-5673 (1990).
Kaplan, et al., "In vitro synthesis of infectious poliovirus RNA," Proc. natl., Acad. Sci USA 82:8424-8428 (1985).
Katinger, et al., "Attenuated Influenza virus as a Vector for Mucosal immunization against HIV-1", Vaccines 97:315-319 (1997).
Kato, et al., "Initiation of Sendai virus multiplication from transfected cDNA or RNA with negative or positive sense," Genes to Cells 1:569-579 (1996).
Winter et al, "Cloning of influenza cDNA into M13: the sequence of the RNA segment encoding the A/PR/8/34 matrix protein", NAR 8(9):1965-74(1980).

(56) References Cited

OTHER PUBLICATIONS

Hsia et al, "Relationship Between Surface Antigens of Two Variants of Influenza A (H3N2) Virus, as Revealed by Hemagglutination Inhibition, Kenetic Neutralization, and Neuraminidase Inhibition", Infection & Immunity (Nov. 1980) p. 467-72.
Webster, "Predictions for future Human Influenza Pandemics", J. Infectious Dis., 176 (Supp 1) S14-19(1977).
Suarez et al, "Heterogeneity of the Mutation Rates of Influenza A Viruses: Isolation of Mutator Mutants", J.Virol., 66 (4):2491-94 (1992).
Parvin et al, "Measurement of the Mutation Rates of Animal Viruses: Influenza A Virus and Poliovirus Type 1", J. Virol., 59(2):377-83 (1986).
Cha et al, "Genotypic Stability of Cold-Adapted Influenza Virus Vaccine in an Efficacy Clinical Trial", J. Clinc. Microbiology, 38(2):839845, 8 45 (2000).
Buonagurio et al, "Evolution of Human Influenza A Viruses over 50 Years: Rapid Uniform Rate of Change in NS Gene", Science, 232(4753) 980-2 (1986).
Lopez-Galindez et al, "Heterogeneity Among Influenza H3N2 Isolates Recovered During an Outbreak", Arch. Virol., 85:139-144 (1985).
Brand et al, "Sequential Passage of Influenza virus in Embryonated Eggs or Tissue Culture: Emergence of Mutants", Virology, 107:424-33 (1980).
Li et al, "Complementation and analysis of an NP mutant of influenza virus", Virus Res. 12(2):97-111 (1989).
Pleschka, et al., "A Plasmid-based Reverse Genetics System for Influenza A Virus," Journal of Virology, vol. 70, No. 6, p. 4188-4192 (1996).
Radecke, et al., "Rescue of measles viruses from cloned DNA," The EMBO journal 14:5773-5784 91995).
Radecke, et al., "Reverse genetics Meets the Nonsegmented negative-Strand RNA Viruses," medical Virology 7:49-63 (1997).
Roberts, et al., "Recovery of negative-Strand RNA Viruses from Plasmid DNAs: A Positive Approach Revitalizes a Negative Field," Virology 247:1-6 (1998).
Rose, J. "Positive strands to the rescue again: A segmented negative-strand RNA virus derived from cloned cDNAs," Proc. Natl. Acad. Sci. USA 94:14998-15000 (1996).
Schlesinger, S., "RNA Viruses as Vectors for the Expression of Heterologous Proteins," Molecular biotechnology 3:155-165 (1995).
Schnell, et al., "Infectious rabies viruses from cloned cDNA," The EMBO Journal 13:4195-4203 (1994).
Seong, et al., "A New Method for Reconstituting Influenza Polymerase and RNA in vitro: A Study of the Promoter Elements for cRNA and vRNA Synthesis in vitro and Viral Rescue in Vivo," Virology 186:247-260 (1992).
Sidhu, et al., "Rescue of Synthetic Measles Virus Minireplicons: Measles Genomic Termini Direct Efficient Expression and Propagation of a Reporter Gene," Virology 208:800-807 (1995).
Subbarao, et al., "Sequential Addition of Temperature-Sensitive Missense mutations into the PB2 Gene of Influenza A Transfectant Viruses Can Effect and Increase in Temperature Sensitivty and Attenuation and Permits the Rational Design . . . ," Journal of Virology 69:5969-5977 (1995).
Szewczyk, et al., "Purification, thioredoxin renaturation, and reconsituted activity of the three subunits of the influenza A virus RNA polymerase," Proc. Natl. Acad. Sci USA 85:7907-7911 (1988).
Taylor, et al., "Newcastle Disease Virus fusion Protein expressed in a Fowlpox Virus Recombinant Confers Protection in chickens," Journal of Virology 64:1441-1450 (1990).
Ward, et al., "Direct measurement of the Poliovius RNA Polymerase Error Frequency in Vitro," Journal of Virology 62:558-562 (1988).
Whelan, et al., "Efficient recovery of infectious vesicular stomatitis virus entirely from cDNA clones" Proc. Natl. Acad. Sci. USA 92:8388-8392 (1995).
Yamanaka, et al., "In vivo analysis of the promoter structure of the influenza virus RNA genome using a transfection system with an engineered RNA," Proc. Natl. Acad. Sci. USA (1991).
Yu, et al., "Functional cDNA Clones of the Human Respiratory Syncytial (RS) Virus N,P, and L Proteins Support Replication of RS Virus Genomic RNA Analogs and Define Minimal trans-Acting Requirements for RNA Replication," Journal of Virology 69:2412-2419 (1995).
Yusoff, et al., "Nucleotide sequence analysis of the L gene of new castle disease virus: homologies with Sendal and vesicular stomatitis viruses," Nucleic Acids Research 15:3961-3976 (1987).
Zaghouani, et al., "Induction of antibodies to the envelope protein of the human immunodeficiency virus by immunization with monoclonal anti-idiotypes," Proc. natl. Acad. Sci. USA 88:5645-5649 (1991).
Zaghouani, et al., "Cells expressing an h Chain Ig Gene Carrying a Viral T Cell Epitope are Lysed by Specific Cytolytic T Cells," The Journal of immunology 148:3604-3609 (1992).
Zhang, et al., "Expression of Functional Influenza virus a Polymerase Proteins and Template from Cloned cDNAs in Recombinant Vaccina Virus Infected cells," Biochemical and Biophysical Research Communications 200:95-101 (1994).
Zobel, et al., "RNA polymerase I catalysed transcription of insert viral cDNA," Nucleic Acids Research 21:3607-3614 (1993).
Ogawa, et al., "Rescue of Akabane virus (family Bunyaviridae) entirely from cloned cDNs by using RNA polymerase I", Journal of General Virology, 88:3385-3390 (2007).
Kaverin, et al, "Impairment of Multicycle Influenza virus Growth in vero (WHO) Cerlls by Loss of Trypsin Activity", Journal of Virology, 69:2700-2703 (1995).
Swain, et al., "Manipulation of Immune Responses Via Particle-mediated Polynucelotide Vaccines", Behring Institute Mitteilungens, 98:73-78 (1997).
International Search Report dated Jun. 4, 2007 for PCT/US2005/041991.
McGeoch, et al., "Influenza virus genome consists of eight distinch species," 1976, vol. 73, p. 3045-49.
Shapiro, et al., "Influenza virus gene expression: control mechanisms at early and late times of infection and nuclear-cystoplasmic transport of virus-specific RNAs," 1987, 61:764-773.
Ishii, et al., "Simultaneous expression of guinea pig UDP-gucuronosyltransferase 2B21 and 2B22 in COS-7 cells enhances UDP-glucuronosyltransferase 2B21-catalyzed morphine-6-glucuronide formation," 2001, 60:1040-1048.
Dewit, J. Gen. Virol., 2007, vol. 88, p. 1281-1287.
Jasenosky, et al. "Ebola virus VP40-induced particle formation and association with the lipid bilayer," 2001, 75:5205-5214.
Pappas, et al., "Single gene reassortants identify a critical ro 2008le for PB1, HA and NA in the high virulence of the 1918 pandemic influenza virus," 2008, 105: 3064-3069.
Reid, et al., "Characterization of the 1918 "Spanish" influenza virus neuraminidase gene," 2000, PNAS, 97:6785-6790.
Schnapp, et al., "Isolation and funcational characterization of TIF-IB, a factor that confers promoter specificity to mouse RNA polymerase I," 1990, 18:1385-1393.
Heix, et al., "Species specificity of transcription by RNA polymerase I," Curren Opinion in Genetics & Devel., 1995, 5:652-656.
Hamzawi, et al., "Antigenicity in hamsters of inactivated vaccines prepared from recombinant influenza viruses," J. Hug (Lond)., 87(3):453-64 (1981).
Schreier et al, "Evolution of influenza polymerase: nucleotide sequence of the PB 2 gene of A/Chile/1/83 (H1N1)," Arch Virol 103:179-187 (1988).
Odagiri et al, "Nucleotide sequence of the PA gene of influenza A/WSN/33(H1N1)," Nucleic Acids Research, 18:654(1990).
Klimov et al, "Correlation of amino acid residues in the M1 and M2 proteins of influenza virus with high yielding properties," Virus Research 19:105-114 (1991).
Jones et al, "The sequence of RNA segment 1 of influenza virus A/NT/60/68 and its comparison with the corresponding sequent of strains A/PR/8/34 and A/WSN/33," Nucleic Acids Research 11:1555-1566 (1983).
Jabbar et al, "Influenza viral (A/WSN/33) hemagglutinin is expressed and glycosylated in the yeast Saccharomyces cerevisiae," Proc. Natl. Acad. Sci. USA 83:2019-2023 (1985).

(56) References Cited

OTHER PUBLICATIONS

Hiti et al, "Complete Nucleotide Sequence of the Neuraminidase Gene of Human Influenza Virus A/WSN/33," Journal of Virology, 41:730-734 (1982).
Davis et al, "Construction and characterization of a bacterial clone containing the hemagglutinin gene of the WSN strain (HON1) of influenza virus," Gene 10:305-218 (1980).
"Schematic presentation of influenza virus replication," copies from http://www.microbiologybites.com, "myxoviruses" (updated Aug. 14, 2008).
Brooks et al, "Orthomyxoviruses (Influenza Viruses)," Jawetz, Melnick & Adelberg's Medical Microbiology, 23rd Edition, Chapter 39, pp. 536-547 (2004).
"Myxoviruses," copied from http://www.microbiologybytes.com (updated Aug. 14, 2008).
Neumann et al, J. of General virology, 76:1709-1717 (1995).
Neumann et al, virology, 2002:477-479 (1994).
Neumann Thesis, Thesis entitled "RNA-Polymerase I Transcription From Influenza cDNA-construction in vitro and in vivo" (Dec. 1992).
Hoffman et al, "A DNA Transfection System for Generation of Influenza A virus from Eight Plasmids," PNAS, May 23, 2000, 97(11):6108-6113.
Muster et al, "Mucosal Model of Immunization against Human Immunodeficiency Virus Type 1 with a Chimeric Influenza Virus," Journal of Virology, 1995, 69(11):6678-6686.
Staczek et al, "A Chimeric Influenza virus Expressing an Epitope of Outer Membrane protein F of Pseudomonas aeruginosa Affords Protection against Challenge with P. aeruginosa in a Murine Model of Chronic Pulmonary Infection," Infection and Immunity, 1998, 66(8):3990-3994.
Friedmann et al (Mar. 5, 1996) "Different interleukin 2 receptor B-chain tyrosines couple to at least two signaling pathways and synergistically mediate interleukin 2-induced proliferation," PNAS USA 93(5):2077-2082.
Hoffman et al, "A DNA Transfection System for Generation of Influenza A Virus: vRNA and mRNA Synthesis from One Template," (May 23, 2000) Virology 267:310-317.
Hoffman et al, "Eight-Plasmid System for Rapid Generation of Influenza virus Vaccines," (2002) Vaccine 20:3165-3170.
Kobasa et al, "Neuraminidase Hemadsorption Activity, Conserved in Avian Influenza A viruses, does not Influence Viral Replication in Ducks," (Sep. 1997) Journal of Virology 71(9):6706-6713.
Neumann et al, "A Decade After the Generation of a Negative-Sense RNA Virus from Cloned cDNA—What Have We Learned?" Journal of General virology 83(11):2635-2662.
Neumann et al, "Plasmid-Driven Formation of Influenza Virus-Like Particles," (Jan. 2000) Journal of Virology 74(1):547-551.
Kimura, et al., "Transcription of a recombinant influenza virus RNA in cells that can express the influenza virus RNA polymerase and nucleoprotein genes," Journal of general Virology 73:1321-1328 (1992).
Kimura, et al., "An In Vivo Study of the Replication Origin in the Influenza Virus complementary RNA," J. Biochem, 113:88-92 (1993).
Kobayashi, et al., "Reconstituion of influenza virus RNA polymerase from three subunits expressed using recombinant baculovirus system" Virus Research 22:235-245 (1992).
Konarska, et al., "Struture of RNAs Replicated by the DNA-Dependent T7 RNA Polymerase," Cell 63:609-618 (1990).
Krystal, et al., "Expression of the three influenza virus polymerase proteins in a single cell allows growth complementation of viral mutants," Proc. Natl. Acad. Sci., USA 83:2709-2713 (1986).

Kunkel, T., "Rapid and efficient site-specific mutagenesis without phenotypic selection," Proc. Natl. Acad. Sci., USA 82:488-492 (1985).
Lamb, et al, "Paramyoxoviridae: The Viruses and their Replication," Fundamental Virology 20:577-647 (1996).
Lawson, et al., "Recombinant vesicular stomatitis viruses from DNA," Proc. Natl. Acad. Sci., USA 92:4477-4481 (1995).
Levis, et al., "Deletion Mapping of Sindbis Virus DI RNAs Derived from cDNA Defines the Sequences Essential for replication and Packaging," Cell 44:137-145 (1986).
Luytjes et al., "Amplification, Expression, and Packaging of a Foreign gene by influenza Virus," Cell 59:1107-1113 (1989).
Mena, et al., "Synthesis of biologically active influenza virus core proteins using a vaccinia virus-T7 RNA polymerase expression system," Journal of general virology 75:2109-2114 (1994).
Mena, et al., "Resue of Synthetic Chloramphenicol Acetyltransferase RNA into Influenza Virus-Like Particles Obtained from Recombinant Plasmids," Journal of Virology 70:5016-5024 (1996).
Moyer, et al., "Assembly and Transcription of Synthetic Vesicular Stomatitis Virus Nucleocapsids," journal of Virology 65:2170-2178 (1991).
Muster, et al., "An influenza A virus containg influenza B virus 5' and 3' noncoding regions on the neuramidinase gene is attenuated in mice," Proc. Natl. Acad. Sci. USA 88:5177*-5171 (1991).
Naito, et al., "Function and Structure of RNA Polymerase from vesicular Stomatitis Virus," the journal of Biological Chemistry, 251:4307-4314 (1976).
Nara, et al., "Simple, Rapid, Quantitative, Syncytium-Forming Microassay for the Detection of Human Immunodeficiency Virus Neutralizing Antibody," AIDS Research and Human retroviruses 3:283:-302 (1987).
Nemeroff, et al., "Influenza Virus NS1 protein interacts with the Cellular 30 kDA Subunit of CPSF and Inhibits 3' End Formatin of cellular Pre-mRNAs," Molecular Cell 1:991-1000 (1998).
Neumann, et al., "RNA Polymerase 1-Mediated Expression of Influenza Viral RNA Molecules," Virology 202:477-479 (1994).
Neumann, et al., "Generationo f influenza A viruses entirely from cloned cDNAs," Proc. natl. Acad. Sci. USA 96:9345-9350 (1999).
Palese, et al., "Negative-strand RNA viruses: Genetic engineering and applications," Proc. Natl. Acad. Sci., USA 93:11354-11358 (1996).
Park, et al., "Rescue of a foreign gene by Sendai virus," Proc. Natl. Acad. Sci. USA 88:5537-5541 (1991).
Pattnaik, et al., "Cells that express all five proteins of vesicular stomatitis virus from cloned cDNAs support replication, assembly and budding of defective interfering particles," Proc. Natl. Acad. Sci. USA 88:1379-1385 (1991).
Peeters, et al., "Resue of new castle Disease Virus from Cloned cDNA: Evidence that Cleavability of the Fusion Protein is a major Determinant for Virulence," Journal of Virology 83:5001-5009 (1999).
Pekosz, et al., "Reverse genetics of negative-strand RNA viruses: Closing the circle," Proc. natl. Acad. Sci. USA 96:8804-8806 (1999).
Percy, et al., "Expression of a Foreign Protein by Influenza A Virus," Journal of Vriology 68:4486-4492 (1994).
Qui, et al., "The Influenza Virus NS1 Protein is a Poly(1)-Binding Protein that Inhibits nuclear Export of mRNAs Containing Poly(A)," Journal of Viruology 68:2425-2432 (1994).
Qui, et al., "The Influenza virus NS1 protein binds to a specific region in human U6 snRNA and inhibits U6-U2 and U6-U4 snRNA interactions during splicing," RNA 1:304-316 (1994).
Racaniello, et al., "Cloned Poliovirus Complementary DNA is Infectious in Mammalian Cells," Science 214:916-919(1981).

PolI-5'WPB2 (15)
CAC ACA *CGT CTC* GTA TTA GTA GAA ACA AGG TCG TTT TTA AAC TAT TCG
ACA CTA ATT GAT GGC CAT CCG AAT TCT TTT GG
Length: 80 nt          Overlap: 26 nt PolI-3'WPB2 (16)
CAC ACA *CGT CTC* CGG GAG CGA AAG CAG GTC AAT TAT ATT CAA TAT GGA
AAG AAT AAA AGA ACT AAG G
Length: 67 nt          Overlap: 24 nt PolI-5'WPB1 (17)
CAC ACA *CGT CTC* GTA TTA GTA GAA ACA AGG CAT TTT TTC ATG AAG GAC
AAG CTA AAT TCA CTA TTT TTG CCG TCT GAG CTC TTC AAT GG
Length: 89             Overlap: 26 nt PolI-3'WPB1 (18)
CAC ACA *CGT CTC* CGG GAG CGA AAG CAG GCA AAC CAT TTG AAT GGA TGT
CAA TCC GAC TTT ACT TTT C
Length: 67 nt          Overlap: 27 nt PolI-5'WPA (19)
CCA ACC *CGT CTC* CTA TTA GTA GAA ACA AGG TAC TTT TTT GGA CAG TAT
GGA TAG CAA ATA GTA GCA TTG CCA CAA CTA TCT CAA TGC ATG TGT GAG
GAA GGA G
Length:103             Overlap: 25 nt PolI-3'WPA (20)
CCA ACC *CGT CTC* CGG GAG CGA AAG CAG GTA CTG ATT CAA AAT GGA AGA
TTT TGT GCG ACA ATG CTT C
Length: 67 nt          Overlap: 27 nt PolI-5'WHA (21)
CAC ACA *CGT CTC* CTA TTA GTA GAA ACA AGG GTG TTT TTC C
Length: 40 nt          Overlap: 22 nt PolI-3'WHA (22)
CAC ACA *CGT CTC* CGG GAG CAA AAG CAG GGG AAA AT  AAA AAC AAC C
Length: 46 nt          Overlap: 29 nt

FIG. 6A

PolI-5'WNP(23)
CAC ACA CGT CTC CTA TTA GTA GAA ACA AGG GTA TTT TTC TTT AAT TG
Length: 47 nt                    Overlap: 30 nt PolI-3'WNP(24)
CAC ACA CGT CTC CGG GAG CAA AAG CAG GGT AGA TAA TCA CTC
Length: 42 nt                    Overlap: 26 nt PolI-5'WNA(25)
CAC ACA CGT CTC CTA TTA GTA GAA ACA AGG AGT TTT TTG AAC AAA C
Length: 46 nt                    Overlap: 29 nt PolI-3'WNA(26)
CAC ACA CGT CTC CGG GAG CGA AAG CAG GAG TTT AAA TGA ATC CAA ACC
Length: 48 nt                    Overlap: 32 nt PolI-5'WM(27)
CAC ACA CGT CTC CTA TTA GTA GAA ACA AGG TAG TTT TTT ACT CCA GC
Length: 47 nt                    Overlap: 30 nt PolI-3'WM(28)
CAC ACA CGT CTC CGG GAG CAA AAG CAG GTA GAT ATT GAA AG
Length: 41 nt                    Overlap: 26 nt PolI-5'WNS (29)
CAC ACA CGT CTC CTA TTA GTA GAA ACA AGG GTG TTT TTT ATT ATT AAA TAA GC
Length: 53 nt                    Overlap: 36 nt PolI-3'WNS (30)
CAC ACA CGT CTC CGG GAG CAA AAG CAG GGT GAC AAA GAC ATA ATG G
Length: 46 nt                    Overlap: 30 nt Italics:            BsmBI recognition sequence
Underlined:         Influenza virus sequence
Underlined + Bold:  Influenza virus coding region

FIG. 6B

SEQUENCE LISTING

```
<160> NUMBER OF SEQ ID NOS: 30

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:plasmid
      sequence

<400> SEQUENCE: 1
gggttattgg agacggtacc gtctcctccc ccc                                   33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:plasmid
      sequence

<400> SEQUENCE: 2
cccaataacc tctgccatgg cagaggaggg ggg                                   33

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:end of PCR
      product
<220> FEATURE:
<221> NAME/KEY: unsure
<222> LOCATION: (7)
<223> OTHER INFORMATION: can be any nucleotide

<400> SEQUENCE: 3
cgtctcntat tagtagaa                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:end of PCR
      product
<220> FEATURE:
<221> NAME/KEY: unsure
<222> LOCATION: (7)
<223> OTHER INFORMATION: can be any nucleotide

<400> SEQUENCE: 4
gcagagnata atcatctt                                                    18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:end of PCR
      product
```

```
<220> FEATURE:
<221> NAME/KEY: unsure
<222> LOCATION: (11)
<223> OTHER INFORMATION: can be any nucleotide

<400> SEQUENCE: 5
ttttgctccc ngagacg                                                  17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:end of PCR
      product
<220> FEATURE:
<221> NAME/KEY: unsure
<222> LOCATION: (11)
<223> OTHER INFORMATION: can be any nucleotide

<400> SEQUENCE: 6
aaaacgaggg nctctgc                                                  17

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence:end of
      restriction enzyme digestion product

<400> SEQUENCE: 7
tattagtaga a                                                        11

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence:end of
      restriction enzyme digestion product

<400> SEQUENCE: 8
aaaacgaggg                                                          10

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:end of
      ligation reaction product

<400> SEQUENCE: 9
gggttattag tagaa                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:end of
      ligation reaction product

<400> SEQUENCE: 10
cccaataatc atctt                                                    15
```

```
<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence:end of
      ligation reaction product

<400> SEQUENCE: 11
ttttgctccc ccc                                                              13

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence:end of
      ligation reaction product

<400> SEQUENCE: 12
aaaacgaggg ggg                                                              13

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:plasmid
      sequence
<220> FEATURE:
<221> NAME/KEY: misc_feature
<222> LOCATION: (1)..(5)
<223> OTHER INFORMATION: 5' RNA polymerase I terminator
<220> FEATURE:
<221> NAME/KEY: misc_feature
<222> LOCATION: (6)..(28)
<223> OTHER INFORMATION: NP-NTR (5' end of vRNA)

<400> SEQUENCE: 13
ttattagtag aaacaagggt attttttct                                             28

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence:plasmid
      sequence
<220> FEATURE:
<221> NAME/KEY: misc_feature
<222> LOCATION: (1)..(39)
<223> OTHER INFORMATION: NP-NTP (3' end of vRNA)
<220> FEATURE:
<221> NAME/KEY: misc_feature
<222> LOCATION: (40)..(43)
<223> OTHER INFORMATION: 3' end RNA polymerase I terminator

<400> SEQUENCE: 14
gatgtcactc agtgagtgat tatctaccct gtttctactc ccc                             43

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
```

```
<220> FEATURE:
<221> NAME/KEY: misc_feature
<222> LOCATION: (18)..(80)
<223> OTHER INFORMATION: Influenza virus sequence

<400> SEQUENCE: 15
cacacacgtc tcgtattagt agaaacaagg tcgttttttaa actattcgac actaattgat       60
ggccatccga attcttttgg                                                    80

<210> SEQ ID NO 16
<211> LENGTH: 67
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(67)
<223> OTHER INFORMATION: Influenza virus sequence

<400> SEQUENCE: 16
cacacacgtc tccgggagcg aaagcaggtc aattatattc aatatggaaa gaataaaaga       60
actaagg                                                                 67

<210> SEQ ID NO 17
<211> LENGTH: 89
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(89)
<223> OTHER INFORMATION: Influenza virus sequence

<400> SEQUENCE: 17
cacacacgtc tcgtattagt agaaacaagg catttttttca tgaaggacaa gctaaattca       60
ctatttttgc cgtctgagct cttcaatgg                                         89

<210> SEQ ID NO 18
<211> LENGTH: 67
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(67)
<223> OTHER INFORMATION: Influenza virus sequence

<400> SEQUENCE: 18
cacacacgtc tccgggagcg aaagcaggca aaccatttga atggatgtca atccgacttt       60
actttttc                                                                67
```

```
<210> SEQ ID NO 19
<211> LENGTH: 103
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(103)
<223> OTHER INFORMATION: Influenza virus sequence

<400> SEQUENCE: 19
ccaacccgtc tcctattagt agaaacaagg tactttttg gacagtatgg atagcaaata      60
gtagcattgc cacaactatc tcaatgcatg tgtgaggaag gag                     103

<210> SEQ ID NO 20
<211> LENGTH: 67
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(67)
<223> OTHER INFORMATION: Influenza virus sequence

<400> SEQUENCE: 20
ccaacccgtc tccgggagcg aaagcaggta ctgattcaaa atggaagatt ttgtgcgaca     60
atgcttc                                                              67

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(40)
<223> OTHER INFORMATION: Influenza virus sequence

<400> SEQUENCE: 21
cacacacgtc tcctattagt agaaacaagg gtgttttcc                            40

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(45)
<223> OTHER INFORMATION: Influenza virus sequence
```

-continued

<400> SEQUENCE: 22
cacacacgtc tccgggagca aaagcagggg aaaataaaaa caacc                45

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(47)
<223> OTHER INFORMATION: Influenza virus sequence

<400> SEQUENCE: 23
cacacacgtc tcctattagt agaaacaagg gtattttct ttaattg                47

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(42)
<223> OTHER INFORMATION: Influenza virus sequence

<400> SEQUENCE: 24
cacacacgtc tccgggagca aaagcagggt agataatcac tc                42

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(46)
<223> OTHER INFORMATION: Influenza virus sequence

<400> SEQUENCE: 25
cacacacgtc tcctattagt agaaacaagg agtttttga acaaac                46

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(48)
<223> OTHER INFORMATION: Influenza virus sequence

<400> SEQUENCE: 26
cacacacgtc tccgggagcg aaagcaggag tttaaatgaa tccaaacc          48

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(47)
<223> OTHER INFORMATION: Influenza virus sequence

<400> SEQUENCE: 27
cacacacgtc tcctattagt agaaacaagg tagtttttta ctccagc          47

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(41)
<223> OTHER INFORMATION: Influenza virus sequence

<400> SEQUENCE: 28
cacacacgtc tccgggagca aaagcaggta gatattgaaa g          41

<210> SEQ ID NO 29
<211> LENGTH: 53
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (18)..(53)
<223> OTHER INFORMATION: Influenza virus sequence

<400> SEQUENCE: 29
cacacacgtc tcctattagt agaaacaagg gtgtttttta ttattaaata agc          53

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_feature
<222> LOCATION: (7)..(12)
<223> OTHER INFORMATION: BsmBI recognition sequence
<220> FEATURE:
<221> NAME/KEY: misc_feature
<222> LOCATION: (17)..(46)
<223> OTHER INFORMATION: Influenza virus sequence -continued

<400> SEQUENCE: 30
cacacacgtc tccgggagca aaagcagggt gacaaagaca taatgg 46

REASSORTANT INFLUENZA VIRUSES FOR VACCINES

STATEMENT OF GOVERNMENT RIGHTS

This invention was made with government support under AIO29599 awarded by the National Institutes of Health. The government has certain rights in the invention.

This application is a Continuation of U.S. application Ser. No. 12/718,573, filed Mar. 5, 2010; which is a Continuation of Ser. No. 09/971,372 filed Oct. 4, 2001, which is a Continuation of International Patent Application No. PCT/US00/09021, filed Apr. 5, 2000; which is an international filing of U.S. Provisional Application No. 60/127,912, filed Apr. 6, 1999, and U.S. Provisional Application No. 60/132,839, filed May 6, 1999; the disclosure of all of which are incorporated by reference.

BACKGROUND OF THE INVENTION

The ability to generate infectious RNA viruses from cloned cDNAs has contributed greatly to the biological understanding of these pathogens and hence to improved methods of disease control (Palese et al., 1996). However, this progress had been relatively limited for negative-sense as compared with positive-sense RNA viruses, because neither the genomic viral RNA (vRNA) nor the antigenomic complementary RNA (cRNA) of negative-sense RNA viruses can serve as a direct template for protein synthesis. Rather, the vRNA, after its encapsidation by viral nucleoprotein (NP), must be transcribed into positive-sense mRNA by the viral RNA polymerase complex. Thus, the minimal replication unit is formed by the genomic vRNA complexed with NP and the polymerase proteins. Despite these obstacles, reverse genetics methods have been established to produce nonsegmented negative-sense RNA viruses, including rabies virus (Snell et al., 1994), vesicular stomatitis virus (Lawson et al., 1995); Whelan et al., 1995), measles virus (Radecke et al., 1995), respiratory syncytial virus (Collins et al., 1995), Sendai virus (Garcin et al., 1995; Kato et al., 1996), rinderpest virus (Baron et al., 1997), human parainfluenza virus type 3 (Hoffman et al., 1997) and SV5 (He et al., 1997).

The Orthomyxoviridae, Arenaviridae, and Bunyaviridae families contain segmented, negative strand RNA genomes and include several human and animal pathogens, for example, influenza virus types A, B, and C (Orthomyxoviridae), lymphocytic choriomeningitis virus (LCMV) (Arenaviridae), and encephalitic and hemorrhagic fever viruses (Bunyaviridae, Arenaviridae). Their genomes consist of two (Arenaviridae), three (Bunyaviridae), or six to eight (Orthomyxoviridae) single-stranded RNA molecules of negative polarity (complementary to mRNA). The vRNAs interact with NP and viral RNA-dependent RNA-polymerase to form ribonucleoprotein complexes (RNPs). The RNPs are surrounded by a lipid bilayer derived from the host cell. Inserted in this envelope are viral glycoproteins, which are essential for receptor binding and entry into the host cell. Thus, generating segmented negative-sense RNA viruses from cloned cDNAs poses a formidable challenge, as one must produce a separate vRNA for each gene segment.

Bridgen and Elliott (1996) produced a Bunyamwera virus (family Bunyaviridae) from cloned cDNAs encoding three segments of antigenomic, positive-sense vRNA. However, the efficiency of virus recovery was low. None of the orthomyxoviruses, which contain six (thogotovirus), seven (influenza C virus) or eight (influenza A and B viruses) segments of negative-sense RNA have been produced entirely from cloned cDNAs. This lag in progress has been felt most acutely in efforts to control influenza virus infections.

Palese and colleagues (Enami et al., 1990) pioneered the reverse genetics, helper virus-dependent system for influenza A virus (FIG. 1A). In their approach, RNP complexes are generated by in vitro vRNA synthesis in the presence of purified polymerase and NP proteins, and then used to transfect eukaryotic cells. Subsequent infection with influenza A helper virus results in the generation of viruses possessing a gene derived from cloned cDNA. A second method, developed by Neumann et al. (1994), is based on the in vivo synthesis of vRNA by RNA polymerase I (FIG. 1B), a cellular enzyme that transcribes ribosomal RNA that lacks both a 5' cap and a 3' polyA tail. Cells infected with influenza virus and transfected with a plasmid containing cloned influenza virus cDNA, flanked by murine RNA polymerase I promoter and terminator sequences, led to the production of transfectant viruses. With both methods, however, transfectants must be selected from a vast background of helper viruses, which requires a strong selection system and complicates the generation of growth-defective viruses.

A system to generate replication-incompetent virus-like particles (VLPs) was developed by Mena et al. (1996), in which an influenza virus-like vRNA encoding a reporter gene is transcribed in vitro and transfected into eukaryotic cells. All ten influenza virus proteins are expressed from plasmids under the control of a T7 RNA polymerase promoter. When the transfected cells are infected with a recombinant vaccinia virus that expressed T7 RNA polymerase, they produced influenza VLPs. However, the efficiency of the system is low: in 25% of the experiments, the investigators failed to detect reporter gene expression. Moreover, vaccinia virus expresses more than 80 proteins, any of which could affect the influenza viral life cycle.

Thus, what is needed is a method to prepare segmented, negative strand RNA viruses, e.g., orthomyxoviruses such as influenza A viruses, entirely from cloned cDNAs.

SUMMARY OF THE INVENTION

The invention provides at least one of the following isolated and purified vectors: a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a operably linked to an influenza virus NS cDNA linked to a transcription termination sequence. The cDNA may be in the sense or antisense orientation relative to the promoter. Thus, a vector of the invention may encode an orthomyxovirus protein (sense), or vRNA (antisense). Any promoter may be employed to express a viral protein. Preferred promoters for the vectors encoding vRNA include, but are not limited to, a RNA polymerase I promoter, a RNA polymerase II promoter, a RNA polymerase III promoter, a T7 promoter, and a T3 promoter. It is further preferred that the RNA polymerase I promoter is a human RNA polymerase I promoter. Preferred transcription termination sequences for the vectors encoding vRNA include, but are not limited to, a RNA polymerase I transcription termination sequence, a RNA polymerase II transcription termination sequence, or a RNA polymerase III transcription termination sequence, or a ribozyme. Preferably, the vectors comprise influenza cDNA, e.g., influenza A (e.g., any influenza A gene including any of the 15 HA or 9 NA subtypes), B or C DNA (see Chapters 45 and 46 of Fields *Virology* (Fields et al. (eds.), Lippincott-Raven Publ., Philadelphia, Pa. (1996), which are specifically incorporated by reference herein), although it is envisioned that the gene(s) of any virus may be employed in the vectors or methods of the invention.

The invention provides a composition comprising a plurality of the orthomyxovirus vectors of the invention. In one embodiment of the invention, the composition comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a operably linked to an influenza virus NS cDNA linked to a transcription termination sequence; and b) at least two vectors selected from a vector encoding influenza virus PA, a vector encoding influenza virus PB1, a vector encoding influenza virus PB2, and a vector encoding influenza virus NP. Preferably, the vectors encoding viral proteins further comprise a transcription termination sequence. It is preferred that a promoter for the vectors comprising influenza virus cDNA includes a RNA polymerase I promoter, a RNA polymerase II promoter, a RNA polymerase III promoter, a T7 promoter, and a T3 promoter. It is also preferred that each vector comprising influenza virus cDNA comprises a transcription termination sequence such as a RNA polymerase I transcription termination sequence, a RNA polymerase II transcription termination sequence, or a RNA polymerase III transcription termination sequence, or a ribozyme. Preferably, the vectors comprise influenza DNA, e.g., influenza A, B or C DNA.

More preferably, the composition comprises a plurality of orthomyxovirus vectors, comprising: a) at least two vectors selected from a vector comprising a RNA polymerase I promoter operably linked to an influenza virus PA cDNA linked to a RNA polymerase I transcription termination sequence, a vector comprising a RNA polymerase I promoter operably linked to an influenza virus PB1 cDNA linked to a RNA polymerase I transcription termination sequence, a vector comprising a RNA polymerase I promoter operably linked to an influenza virus PB2 cDNA linked to a RNA polymerase I transcription termination sequence, a vector comprising a RNA polymerase I promoter operably linked to an influenza virus HA cDNA linked to a RNA polymerase I transcription termination sequence, a vector comprising a RNA polymerase I promoter operably linked to an influenza virus NP cDNA linked to a RNA polymerase I transcription termination sequence, a vector comprising a RNA polymerase I promoter operably linked to an influenza virus NA cDNA linked to a RNA polymerase I transcription termination sequence, a vector comprising a RNA polymerase I promoter operably linked to an influenza virus M cDNA linked to a RNA polymerase I transcription termination sequence, and a vector comprising a RNA polymerase I promoter operably linked to an influenza virus NS cDNA linked to a RNA polymerase I transcription termination sequence; and b) at least two vectors selected from a vector encoding influenza virus PA, a vector encoding influenza virus PB1, a vector encoding influenza virus PB2, a vector encoding influenza virus NP, a vector encoding influenza virus HA, a vector encoding influenza virus NA, a vector encoding influenza virus M1, a vector encoding influenza virus M2, and a vector encoding influenza virus NS2.

Another embodiment of the invention comprises a composition of the invention as described above further comprising a vector comprising a promoter linked to 5' orthomyxovirus non-coding sequences linked to a desired linked to 3' orthomyxovirus non-coding sequences linked to transcription termination sequences. The introduction of such a composition to a host cell permissive for orthomyxovirus replication results in recombinant virus comprising vRNA corresponding to sequences of the vector comprising 5' orthomyxovirus non-coding sequences linked to a cDNA linked to 3' orthomyxovirus non-coding sequences. Preferably, the cDNA is in an antisense orientation. Also preferably, the promoter is a RNA polymerase I promoter, a RNA polymerase II promoter, a RNA polymerase III promoter, a T7 promoter, and a T3 promoter. It is also preferred that the transcription termination sequence is a RNA polymerase I transcription termination sequence, a RNA polymerase II transcription termination sequence, or a RNA polymerase III transcription termination sequence, or a ribozyme. For example, the cDNA may encode an immunogenic epitope, such as an epitope useful in a cancer therapy or vaccine.

A plurality of the vectors of the invention may be physically linked or each vector may be present on an individual plasmid or other, e.g., linear, nucleic acid delivery vehicle.

The invention also provides a method to prepare influenza virus. The method comprises contacting a cell with a plurality of the vectors of the invention, e.g., sequentially or simultaneously, for example, employing a composition of the invention, in an amount effective to yield infectious influenza virus. The invention also includes isolating virus from a cell contacted with the composition. Thus, the invention further provides isolated virus, as well as a host cell contacted with the composition or isolated virus of the invention.

As described hereinbelow, influenza A viruses were prepared entirely from cloned cDNAs. The reverse genetics approach described herein is highly efficient and can be used to introduce mutations into any gene segment and to develop influenza virus-based gene delivery systems. For example, human embryonic kidney cells (293T) were transfected with eight plasmids, each encoding a viral RNA of the A/WSN/33 (H1N1) or A/PR/8/34 (H1N1) virus, flanked by the human RNA polymerase I promoter and the mouse RNA polymerase I terminator, together with plasmids encoding viral nucleoprotein and the PB2, PB1 and PA viral polymerases. This strategy yields >$1 \times 10^3$ plaque-forming units (pfu) of virus per ml of supernatant at 48 hours post-transfection. Depending on the virus generated, the addition of plasmids expressing all of the remaining viral structural proteins led to a substantial increase in virus production, >$3 \times 10^4$ pfu/ml. Reverse genetics was also employed to generate a reassortant virus containing the PB1 gene of the A/PR/8/34 virus, with all other genes representing A/WSN/33. Additional viruses produced by this method had mutations in the PA gene or possessed a foreign epitope in the head of the neuraminidase protein.

Moreover, the same approach may be employed for other viruses to generate nonsegmented negative strand RNA viruses (i.e., Paramyxoviridae, Rhabdoviridae, and Filoviridae), or other segmented negative strand RNA viruses, e.g., Arenaviridae and Bunyaviridae, entirely from cloned cDNA. Further, the expression of cRNA in cells instead of vRNA may improve the efficiency of virus generation.

The method of the invention allows easy manipulation of influenza viruses, e.g., by the introduction of attenuating mutations into the viral genome. Further, because influenza viruses induce strong humoral and cellular immunity, the invention greatly enhances these viruses as vaccine vectors, particularly in view of the availability of natural variants of the virus, which may be employed sequentially, allowing repetitive use for gene therapy.

Thus, the invention provides isolated and purified vectors or plasmids, which express or encode influenza virus proteins, or express or encode influenza vRNA, both native and recombinant vRNA. Thus, a vector or plasmid of the invention may comprise a gene or open reading frame of interest, e.g., a foreign gene encoding an immunogenic peptide or protein useful as a vaccine. Preferably, the vector or plasmid which expresses influenza vRNA comprises a promoter, e.g., a RNA polymerase I, suitable for expression in a particular host cell, e.g., avian or mammalian host cells such as canine, feline, equine, bovine, ovine, or primate cells including human cells. Also preferably, the vectors or plasmids comprising DNA useful to prepare influenza vRNA comprise RNA polymerase I transcription termination sequences. For vectors or plasmids comprising a gene or open reading frame of interest, it is preferred that the gene or open reading frame is flanked by the 5' and 3' non-coding sequences of influenza virus, and even more preferably, that the gene or open reading frame is operably linked to a RNA polymerase I promoter and RNA polymerase I transcription termination sequence.

As described hereinbelow, 293T were transfected with plasmids encoding the influenza A virus structural proteins, together with a plasmid that contained the green fluorescence protein (GFP) reporter gene, flanked by an RNA polymerase I promoter and terminator. Intracellular transcription of the latter construct by RNA polymerase I generated GFP vRNA that was packaged into influenza virus-like particles. This system, which produced more than $10^4$ infectious particles per ml of supernatant, may be useful in studies of influenza virus replication and particle formation. It might also benefit efforts in vaccine production and in the development of improved gene therapy vectors.

Therefore, the invention also provides for a host cell, the genome of which is stably augmented with at least one recombinant DNA molecule. The recombinant DNA molecule includes at least one of the following: a recombinant DNA molecule comprising a promoter functional in the host cell linked to a first lox site linked to a DNA segment comprising a transcription stop or termination sequence linked to a second lox site linked to an influenza virus HA coding region; a recombinant DNA molecule comprising a promoter functional in the host cell linked to a first lox site linked to a DNA segment comprising a transcription stop or termination sequence linked to a second lox site linked to an influenza virus NA coding region; a recombinant DNA molecule comprising a promoter functional in the host cell linked to a first lox site linked to a DNA segment comprising a transcription stop or termination sequence linked to a second lox site linked to an influenza virus M1 coding region; a recombinant DNA molecule comprising a promoter functional in the host cell linked to a first lox site linked to a DNA segment comprising a transcription stop or termination sequence linked to a second lox site linked to an influenza virus NS2 coding region; a recombinant DNA molecule comprising a promoter functional in the host cell linked to a first lox site linked to a DNA segment comprising a transcription stop or termination sequence linked to a second lox site linked to an influenza virus M2 coding region; a recombinant DNA molecule comprising a promoter functional in the host cell linked to a first loxP site linked to a DNA segment comprising a transcription stop or termination sequence linked to a second lox site linked to an influenza virus PA coding region; a recombinant DNA molecule comprising a promoter functional in the host cell linked to a first lox site linked to a DNA segment comprising a transcription stop or termination sequence linked to a second lox site linked to an influenza virus PB1 coding region; a recombinant DNA molecule comprising a promoter functional in the host cell linked to a first lox site linked to a DNA segment comprising a transcription stop or termination sequence linked to a second lox site linked to an influenza virus PB2 coding region; or a recombinant DNA molecule comprising a promoter functional in the host cell linked to a first lox site linked to a DNA segment comprising a transcription stop or termination sequence linked to a second lox site linked to an influenza virus NP coding region.

Preferably, the host cell is augmented with a recombinant DNA molecule comprising a promoter functional in the host cell linked to a first lox site linked to a DNA segment comprising a transcription stop sequence linked to a second lox site linked to an influenza virus HA coding region; a recombinant DNA molecule comprising a promoter functional in the host cell linked to a first lox site linked to a DNA segment comprising a transcription stop sequence linked to a second lox site linked to an influenza virus NA coding region; a recombinant DNA molecule comprising a promoter functional in the host cell linked to a first lox site linked to a DNA segment comprising a transcription stop sequence linked to a second lox site linked to an influenza virus M1 coding region; a recombinant DNA molecule comprising a promoter functional in the host cell linked to a first lox site linked to a DNA segment comprising a transcription stop sequence linked to a second lox site linked to an influenza virus NS2 coding region; and a recombinant DNA molecule comprising a promoter functional in the host cell linked to a first lox site linked to a DNA segment comprising a transcription stop sequence linked to a second lox site linked to an influenza virus M2 coding region. Preferably, the lox sites are loxP sites.

The invention also provides a method to prepare infectious replication defective influenza virus. The method comprises contacting a host cell which is augmented with at least one recombinant DNA molecule of the invention, e.g., encoding HA, NA, M1, M2, NS2, PA, PB1, PB2, or NP, with a recombinant influenza virus comprising: vRNA comprising a Cre open reading frame, and vRNAs comprising influenza genes not expressed by the host cell. Virus is then recovered from the contacted host cell. Preferably, the recombinant virus further comprises vRNA comprising a desired open reading frame. Alternatively, the augmented host cell is contacted with a vector comprising a promoter functional in the host cell operably linked to a DNA segment encoding Cre, and a plurality of vectors each comprising a promoter operably linked to an influenza virus cDNA not present in the host cell. Virus is then recovered.

The invention also provides a host cell, the genome of which is augmented with a recombinant DNA molecule comprising a promoter functional in the host cell linked to a first lox site linked to a DNA segment comprising a transcription stop sequence linked to a second lox site linked to a host cell surface binding protein coding region; a recombinant DNA molecule comprising a promoter functional in the host cell linked to a first lox site linked to a DNA segment comprising a transcription stop sequence linked to a second lox site linked to a fusion protein coding region; a recombinant DNA molecule comprising a promoter functional in the host cell linked to a first lox site linked to a DNA segment comprising a transcription stop sequence linked to a second lox site linked to an influenza virus M1 coding region; a recombinant DNA molecule comprising a promoter functional in the host cell linked to a first lox site linked to a DNA segment comprising a transcription stop sequence linked to a second lox site linked to an influenza virus NS2 coding region; and a recombinant DNA molecule comprising a promoter functional in the host cell linked to a first lox site linked to a DNA segment comprising a transcription stop sequence linked to a second lox site linked to an influenza virus M2 coding region. Preferably, the lox sites are loxP sites.

Yet another embodiment is a host cell, the genome of which is augmented with a recombinant DNA molecule comprising a promoter functional in the host cell linked to a first lox site linked to a DNA segment comprising a transcription stop sequence linked to a second lox site linked to a host cell surface binding and fusion protein coding region; a recombinant DNA molecule comprising a promoter functional in the host cell linked to a first lox site linked to a DNA segment comprising a transcription stop sequence linked to a second lox site linked to an influenza virus M1 coding region; a recombinant DNA molecule comprising a promoter functional in the host cell linked to a first lox site linked to a DNA segment comprising a transcription stop sequence linked to a second lox site linked to an influenza virus NS2 coding region; and a recombinant DNA molecule comprising a promoter functional in the host cell linked to a first lox site linked to a DNA segment comprising a transcription stop sequence linked to a second lox site linked to an influenza virus M2 coding region. Preferably, the lox sites are loxP sites.

Host cells augmented with recombinant DNA molecules as described hereinabove are useful to prepare infectious replication defective influenza virus. For example, a host cell stably transformed with recombinant DNA molecules encoding HA, NA, M1, M2 and NS2 is contacted with a plurality of vectors, i.e., vectors which express vRNA comprising a Cre open reading frame, vRNA comprising PA, vRNA comprising NP, vRNA comprising PB1, vRNA comprising PB2, and optionally, vRNA comprising a gene of interest; and vectors which encode PA, PB1, PB2, and NP.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors).

Thus, a virus for use in medical therapy (e.g., for a vaccine or gene therapy) is provided. For example, the invention provides a method to immunize an individual against a pathogen, e.g., a bacteria; virus, or parasite, or a malignant tumor. The method comprises administering to the individual an amount of at least one isolated virus of the invention, optionally in combination with an adjuvant, effective to immunize the individual. The virus comprises vRNA comprising a polypeptide encoded by the pathogen or a tumor specific polypeptide.

Also provided is a method to augment or increase the expression of an endogenous protein in a mammal having an indication or disease characterized by a decreased amount or a lack of the endogenous protein. The method comprises administering to the mammal an amount of an isolated virus of the invention effective to augment or increase the amount of the endogenous protein in the mammal. Preferably, the mammal is a human.

The invention also provides vectors and methods for the recombinant production of positive strand viruses, e.g., positive-sense RNA viruses. Thus, the invention provides a vector comprising a DNA segment comprising RNA polymerase I transcription initiation sequences operably linked to a second DNA segment comprising sequences from a positive-sense RNA virus, optionally operably linked to a third DNA segment comprising RNA polymerase I transcription termination sequences. Also provided is a method of using the vector(s) to prepare recombinant virus. The method is particularly useful as it employs cloned DNA and transfection techniques, thus circumventing RNA handling. Moreover, RNA polymerase I transcription is highly efficient and has high fidelity. For positive-sense RNA viruses whose genomic RNA is uncapped (e.g., pestiviruses; hepatitis C virus; and Picornaviridae, including poliovirus, rhinoviruses, hepatitis A virus, and foot and mouth disease virus), a cDNA encoding the full-length genome is introduced in genomic-sense orientation between RNA polymerase I promoter and terminator sequences. Transfection of the resulting plasmid into permissive host cells yields genomic RNA for virus replication. A number of positive-sense RNA viruses contain capped genomic RNAs (e.g., flaviviruses, including dengue fever virus and several encephalitis viruses). While RNA polymerase I transcripts are not capped, a cDNA encoding the full-length genome of RNA viruses having capped genomic RNAs is introduced in antigenomic-sense orientation in a RNA polymerase I transcription vector. Following transfection of the resulting plasmid, cellular RNA polymerase I transcribes an antigenomic (uncapped) RNA. Moreover, cotransfection with protein expression plasmids for the proteins required for replication results in the replication of the antigenomic RNA, hence yielding genomic RNA and ultimately infectious virus.

BRIEF DESCRIPTION OF THE DRAWINGS

FIGS. 6A and 6B. Primers employed to amplify influenza sequences. The SEQ ID NO for each primer is presented as a numeric number in a parentheses positioned next to the primer.

DETAILED DESCRIPTION OF THE INVENTION

Definitions

Figure 1:
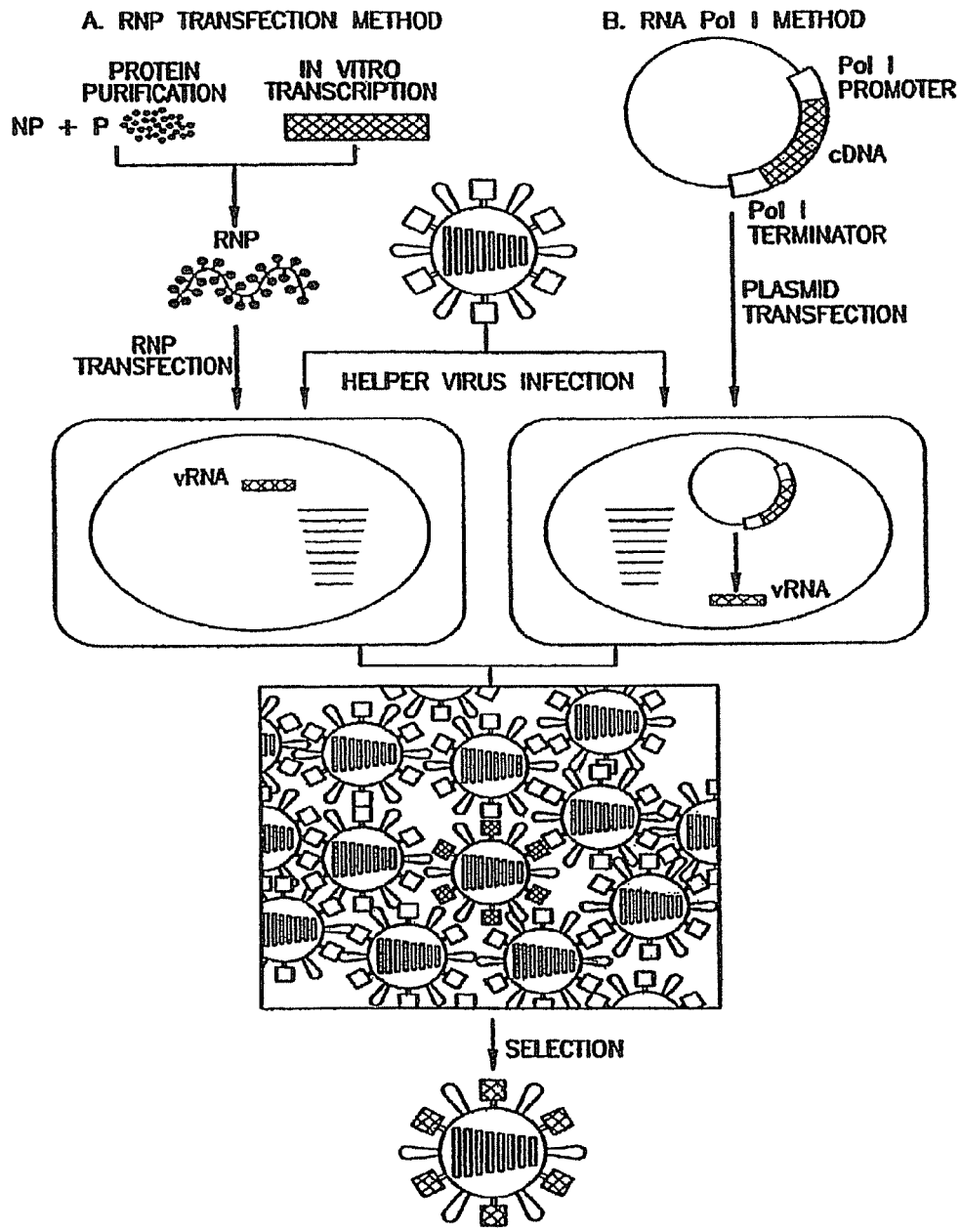
FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. With both methods, transfectant viruses (i.e., those containing RNA derived from cloned cDNA), are selected from the helper virus population.

As used herein, the terms "isolated and/or purified" refer to in vitro preparation, isolation and/or purification of a vector or plasmid of the invention, so that it is not associated with in vivo substances, or is substantially purified from in vitro substances. As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, "site-specific recombination" is intended to include the following three events: 1) deletion of a target DNA segment flanked by site-specific recombination sites or sequences, e.g., loxP sites; 2) inversion of the nucleotide sequence of a target DNA segment flanked by site-specific recombination sites or sequences, e.g., lox sites; and 3) reciprocal exchange of target DNA segments proximate to site-specific recombination sites or sequences, e.g., lox sites located on different DNA molecules. Site-specific recombinase systems include, but are not limited to, the Cre/loxP system of bacteriophage P1 (U.S. Pat. No. 5,658,772).

To remedy the reversibility of a site-specific recombination reaction, the structure of the recombination system may be altered. The site-specific recombination sequence can be mutated in a manner that the product of the recombination reaction is no longer recognized as a substrate for the reverse reaction, thereby stabilizing the integration or excision event. For example, to remove undesired sequences, lox sites in the same orientation are positioned to flank the undesired sequences.

Other lox sites include loxB, loxL, and loxR sites which are nucleotide sequences isolated from *E. coli* (Hoess et al., *Proc. Natl. Acad. Sci. USA,* 79, 3398 (1982)). Lox sites can also be produced by a variety of synthetic techniques which are known in the art. For example, synthetic techniques for producing lox sites are disclosed by Ito et al., *Nuc. Acid Res.*, 10, 1755 (1982) and Ogilvie et al., *Science*, 214, 270 (1981).

As used herein, the expression "lox site" means a nucleotide sequence at which the gene product of the cre gene can catalyze a site-specific recombination. LoxP is a 34 base pair nucleotide sequence which can be isolated from bacteriophage P1 by methods known in the art (see, for example, Hoess et al., *Proc. Natl. Acad. Sci. USA*, 79, 3398 (1982)). LoxP consists of two 13 base pair inverted repeats separated by an 8 base pair spacer region.

As used herein, the expression "cre gene" means a nucleotide sequence which codes for an enzymic gene product which effects site-specific recombination of DNA in eukaryotic cells at lox sites. A cre gene can be isolated from bacteriophage P1 by methods known in the art (see Abremaid et al., *Cell*, 32, 1301-1311 (1983)).

Influenza Virus Replication

Influenza A viruses possess a genome of eight single-stranded negative-sense viral RNAs (vRNAs) that encode a total of ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Thogotovirus

Thogotoviruses (THOV) represent a new genus in the family of Orthomyxoviridae. They are transmitted by ticks and have been found in domestic animals, including camels, goats, and cattle. Consequently, THOV can replicate in tick and vertebrate cells. The THOV genome comprises six segments of single-stranded, negative-sense RNA. The proteins encoded by the three largest segments show significant homology to the influenza virus polymerase proteins PB2, PB1, and PA. Segment 5 encodes a protein related to influenza virus NP. The THOV glycoprotein, which is encoded by segment 4, is not homologous to either influenza virus HA or NA, but it shows sequence similarity to the Baculovirus glycoprotein. The smallest segment is thought to encode a matrix protein and does not resemble any of the influenza virus proteins. Like influenza virus, both the 3' and 5' ends of the vRNA are required for promoter activity, and this activity is located in the terminal 14 and 15 nucleotides of the 3' and 5' ends of the vRNA, respectively.

The mRNA synthesis of THOV is primed by host cell-derived cap structures. However, in contrast to influenza virus, only the cap structures (without additional nucleotides) are cleaved from cellular mRNAs (Albo et al., 1996; Leahy et al., 1997; Weber et al., 1996). In vitro cleavage assays revealed that both the 5' and 3' ends of vRNA are required for endonuclease activity (Leahy et al., 1998), but addition of a model cRNA promoter does not stimulate endonuclease activity (Leahy et al., 1998), as has been shown for influenza virus (Cianci et al., 1995; Hagen et al., 1994). A 'hook' structure has been proposed for THOV (Leahy et al., 1997; Weber et al., 1997), which is similar to the corkscrew structure proposed for influenza virus (Flick et al., 1996). This 'hook' structure, however, is only found in the THOV vRNA promoter. The cRNA promoter sequence does not allow the formation of base pairs between positions 2 and 9, and between 3 and 8 at the 5' end of the cRNA. Alterations at positions 3 or 8 to allow base-pairing between these nucleotides stimulates endonuclease activity, which is strong supporting evidence of the proposed 'hook' structure (Leahy et al., 1998). Moreover, this structure might be crucial for the regulation of the THOV life cycle; the vRNA promoter, forming the 'hook' structure, may stimulate PB2 endonuclease activity, thereby allowing transcription. The cRNA promoter, in contrast, may not form the 'hook' structure and may therefore be unable to stimulate endonuclease activity, thus resulting in replication.

Bunyaviridae

The family Bunyaviridae includes several viruses that cause hemorrhagic or encephalitic fevers in humans (e.g., Rift fever valley, Hantaan, La Crosse, and Crimean-Congo hemorrhagic fever). The spherical and enveloped virions contain three segments of single-stranded, negative-sense RNA (reviewed in Elliott, 1997). The largest segment (L) encodes the viral RNA polymerase protein (L protein), whereas the M segment encodes the two viral glycoproteins G1 and G2, and a nonstructural protein (NSm). The smallest segment (S) encodes the nucleocapsid protein (N) and a second nonstructural protein (NSs). Virus replication and transcription take place in the cytoplasm, and newly assembled virions bud through the membranes of the Golgi apparatus.

Bridgen & Elliott (1996) have established a reverse genetics system to generate infectious Bunyamwera virus entirely from cloned cDNAs. They followed a strategy first described by Schnell et al. (1994) for rabies virus: intracellular transcription of a cDNA coding for the positive-sense antigenomic RNA (but not for the negative-sense genomic RNA) in cells expressing the viral polymerase and nucleoprotein. Bridgen & Elliott (1996) infected HeLaT4+ cells with vaccinia virus expressing T7 polymerase and transfected these cells with plasmids expressing proteins encoded by the S, M, and L segments. They then transfected these cells with three plasmids encoding full-length anti-genomic cDNAs flanked by the T7 polymerase promoter and the hepatitis delta virus ribozyme. To increase the number of bunyavirus particles relative to the number of vaccinia virus particles, the authors used mosquito cells in which Bunyamwera but not Vaccinia virus replicates. This protocol can be used not only to genetically engineer Bunyaviridae, but also generate reassortant viruses that cannot easily be obtained by coinfecting cells with different Bunyaviridae strains.

To study bunyavirus promoter elements and the viral proteins that are required for transcription and replication, Dunn et al. (1995) cloned the CAT gene in the negative-sense orientation between the 5' and 3' nontranslated regions of the Bunyamwera S RNA segment. Cells were transfected with constructs expressing the proteins encoded by the L and S segment and were then transfected with in vitro transcribed RNA, which resulted in CAT activity. The bunyavirus S segment encodes two proteins, N and NSs, in overlapping reading frames. To determine whether both of these proteins are required for transcription and replication, constructs expressing only N or NSs were tested for CAT activity. N protein expression, together with L protein, resulted in CAT activity, whereas no CAT activity was detected with the NSs expression construct. Thus, the L and N proteins are sufficient for transcription and replication of a bunyavirus-like RNA.

As with influenza virus, the terminal sequences of bunyavirus RNAs are complementary and highly conserved. It has therefore been assumed that these sequence elements define the bunyaviral promoter and are crucial for promoter activity. Deletion of five nucleotides at the 3' end of the viral RNA drastically reduces CAT expression (Dunn et al., 1995). In contrast, addition of two nucleotides at the 5' end, or of 11 or 35 nucleotides at the 3' end does not abolish CAT expression (Dunn et al., 1995). Therefore, like the influenza virus polymerase complex, the bunyavirus polymerase protein can apparently start transcription and/or replication internally.

The invention will be further described by the following examples.

Example 1

Materials and Methods

Cells and Viruses.

293T human embryonic kidney cells and Madin-Darby canine kidney cells (MDCK) were maintained in Dulbecco's modified Eagle medium (DMEM) supplemented with 10% fetal calf serum and in modified Eagle's medium (MEM) containing 5% newborn calf serum, respectively. All cells were maintained at 37° C. in 5% $CO_2$. Influenza viruses A/WSN/33 (H1N1) and A/PR/8/34 (H1N1) were propagated in 10-day-old eggs.

Construction of Plasmids.

Figure 2:
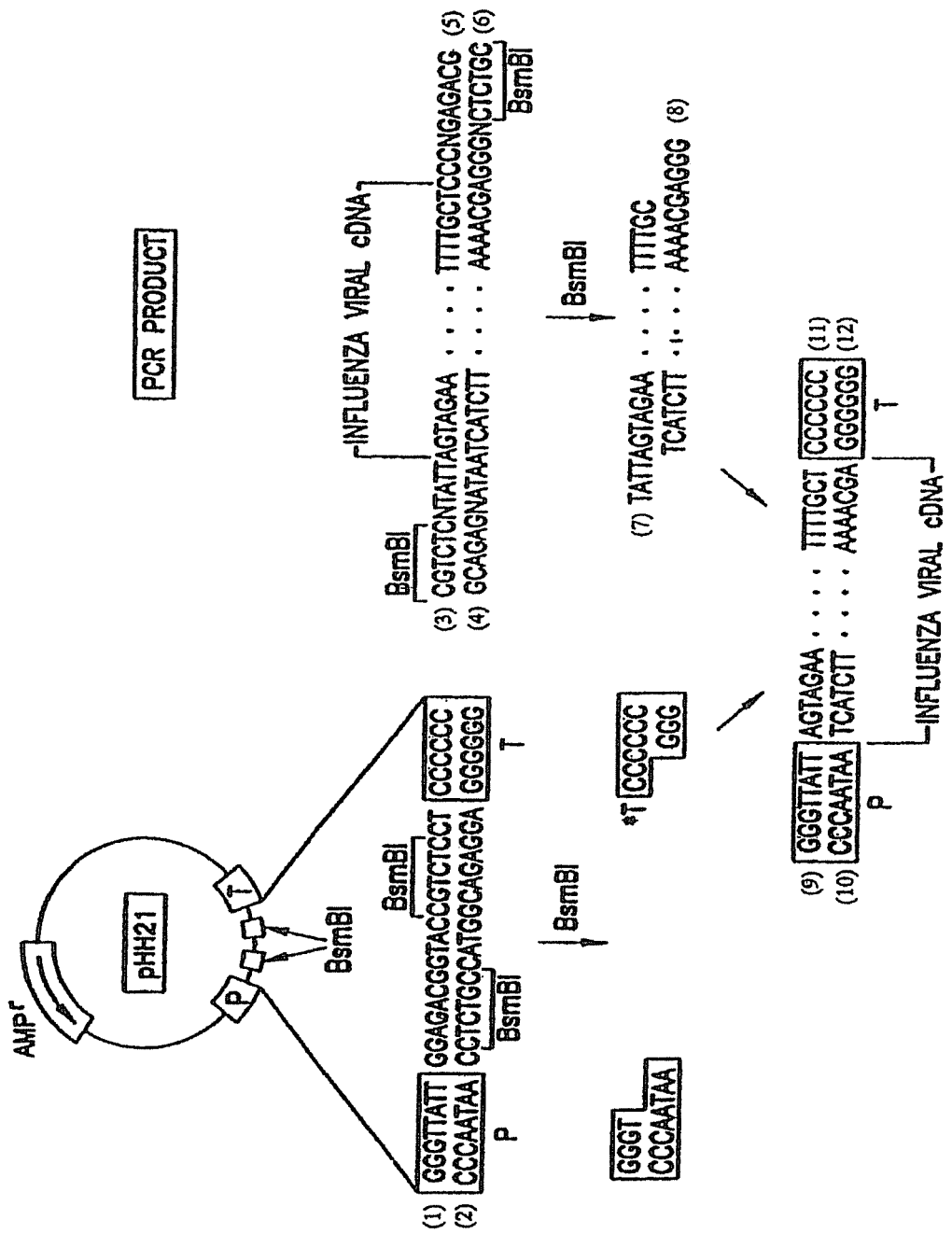
FIG. 2. Schematic diagram of the generation of RNA polymerase I constructs. cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany), which contains the human RNA polymerase I promoter (P) and the mouse RNA polymerase I terminator (T). The thymidine nucleotide upstream of the terminator sequence (*T) represents the 3' end of the influenza viral RNA Influenza A virus sequences are shown in bold face letters. The numeric numbers in parentheses positioned next to the nucleotide sequences represent the SEQ ID NOs for the sequences.

To generate RNA polymerase I constructs, cloned cDNAs derived from A/WSN/33 or A/PR/8/34 viral RNA were introduced between the promoter and terminator sequences of RNA polymerase I. Briefly, the cloned cDNAs were amplified by PCR with primers containing BsmBI sites, digested with BsmBI, and cloned into the BsmBI sites of the pHH21 vector which contains the human RNA polymerase I promoter and the mouse RNA polymerase I terminator, separated by BsmBI sites (FIG. 2). The PB2, PB1, PA, HA, NP, NA, M, and NS genes of the A/WSN/33 strain were PCR-amplified by use of the following plasmids: pSCWPB2, pGW-PB1, and pSCWPA (all obtained from Dr. Debi Nayak at the University of California Los Angeles), and pWH17, pWNP152, pT3WNA15 (Castrucci et al., 1992), pGT3WM, and pWNS 1, respectively. The PB1 gene of influenza A/PR/8/34 virus was amplified by using pcDNA774 (PB1) (Perez et al., 1998) as a template. See FIG. 6 for the sequences of the primers. To ensure that the genes were free of unwanted mutations, PCR-derived fragments were sequences with an autosequencer (Applied Biosystem Inc., CA, USA) according to the protocol recommended by the manufacturer. The cDNAs encoding the HA, NP, NA, and M1 genes of AJWSN/33 virus were cloned as described (Huddleston et al., 1982) and subcloned into the eukaryotic expression vector pCAGGS/MCS (controlled by the chicken β-actin promoter) (Niwa et al., 1991), resulting in pEWSN-HA, pCAGGS-WSN—NP0-14, pCAGGS-WNA15, and pCAGGS-WSN-M1-2/1, respectively. The M2 and NS2 genes from the A/PR/8/34 virus were amplified by PCR and cloned into pCAGGS/MCS, yielding pEP24c and pCA-NS2. Finally, pcDNA774(PB1), pcDNA762(PB2), and pcDNA787(PA) were used to express the PB2, PB1, and PA proteins under control of the cytomegalovirus promoter (Perez et al., 1998).

Generation of Infectious Influenza Particles.

293T cells ($1 \times 10^6$) were transfected with a maximum of 17 plasmids in different amounts with use of Trans IT LT-1 (Panvera, Madison, Wis.) according to the manufacturer's instructions. Briefly, DNA and transfection reagent were mixed (2 μl Trans IT-LT-1 per μg of DNA), incubated at room temperature for 45 minutes and added to the cells. Six hours later, the DNA-transfection reagent mixture was replaced by Opti-MEM (Gibco/BRL, Gaithersburg, Md.) containing 0.3% bovine serum albumin and 0.01% fetal calf serum. At different times after transfection, viruses were harvested from the supernatant and titrated on MDCK cells. Since helper virus was not required by this procedure, the recovered transfectant viruses were analyzed without plaque purification.

Determination of the Percentage of Plasmid-Transfected Cells Producing Viruses.

Twenty-four hours after transfection, 293T cells were dispersed with 0.02% EDTA into single cells. The cell suspension was then diluted 10-fold and transferred to confluent monolayers of MDCK cells in 24-well plates. Viruses were detected by the hemagglutination assay.

Immunostaining Assay.

Nine hours after infection with influenza virus, cells were washed twice with phosphate-buffered saline (PBS) and fixed with 3.7% paraformaldehyde (in PBS) for 20 minutes at room temperature. Next, they were treated with 0.1% Triton X-100 and processed as described by Neumann et al. (1997).

Results

Generation of Infectious Virus by Plasmid-Driven Expression of Viral RNA Segments, Three Polymerase Subunits and NP Protein.

Figure 3:
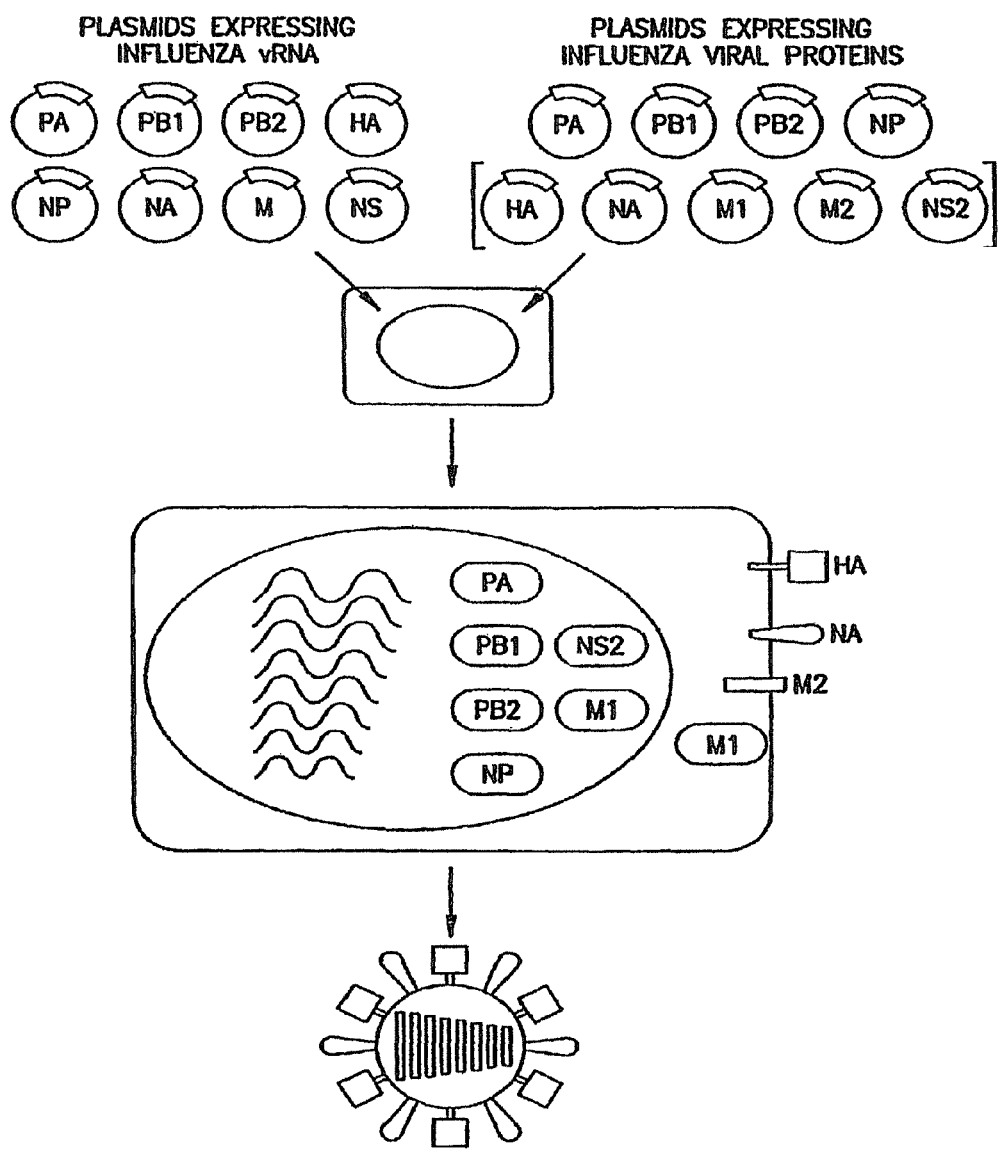
FIG. 3. Proposed reverse genetics method for generating segmented negative-sense RNA viruses. Plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.

Although transfection of cells with a mixture of RNPs extracted from purified virions results in infectious influenza particles, this strategy is not likely to be efficient when used with eight different in vitro generated RNPs. To produce infectious influenza viruses entirely from cDNAs, eight viral RNPs were generated in vivo. Thus, plasmids were prepared that contain cDNAs for the full-length viral RNAs of the A/WSN/33 virus, flanked by the human RNA polymerase I promoter and the mouse RNA polymerase I terminator. In principle, transfection of these eight plasmids into eukaryotic cells should result in the synthesis of all eight influenza vRNAs. The PB2, PB1, PA and NP proteins, generated by cotransfection of protein expression plasmids, should then assemble the vRNAs into functional vRNPs that are replicated and transcribed, ultimately forming infectious influenza viruses (FIG. 3). $1 \times 10^6$ 293T cells were transfected with protein expression plasmids (1 μg of pcDNA762(PB2), 1 μg of pcDNA774(PB1), 0.1 μg of pcDNA787(PA), and 1 μg of pCAGGS-WSN-NP0/14) and 1 μg of each of the following RNA polymerase I plasmids (pPolI-WSN-PB2, pPolI-WSN-PB1, pPolI-WSN-PA, pPolI-WSN-HA, pPolI-WSN-NP, pPolI-WSN-NA, pPolI-WSN-M, and pPolI-WSN-NS). The decision to use a reduced amount of pcDNA787(PA) was based on previous observations (Mena et al., 1996), and data on the optimal conditions for generation of virus-like particles (VLPs) (data not shown). Twenty-four hours after transfection of 293T cells, $7 \times 10^3$ pfu of virus per ml was found in the supernatant (Experiment 1, Table 1), demonstrating for the first time the capacity of reverse genetics to produce influenza A virus entirely from plasmids.

TABLE 1

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| RNA polymerase I plasmids for:[†] | | | | | | | | |
| PB1 | + | + | − | − | − | − | − | − |
| PR8-PB1 | − | − | + | + | + | + | + | + |
| PB2 | + | + | + | + | + | + | + | + |
| PA | + | + | + | + | + | + | + | + |
| HA | + | + | + | + | + | + | + | + |
| NP | + | + | + | + | + | + | + | + |
| NA | + | + | + | + | + | + | + | + |
| M | + | + | + | + | + | + | + | + |
| NS | + | + | + | + | + | + | + | + |
| Protein expression plasmids for: | | | | | | | | |
| PB1 | + | + | + | + | − | + | + | + |
| PB2 | + | + | + | + | + | − | + | + |
| PA | + | + | + | + | + | + | − | + |
| NP | + | + | + | + | + | + | + | − |
| HA | − | + | − | + | + | + | + | + |
| NA | − | + | − | + | + | + | + | + |
| M1 | − | + | − | + | + | + | + | + |
| M2 | − | + | − | + | + | + | + | + |
| NS2 | − | + | − | + | + | + | + | + |
| Virus titer (pfu/ml) | $7 \times 10^3$ | $7 \times 10^3$ | $1 \times 10^3$ | $3 \times 10^4$ | 0 | 0 | 0 | 0 |

*293T cells were transfected with the indicated plasmids. Twenty-four (Experiments 1 and 2) or forty-eight hours (Experiments 3-8) later, the virus titer in the supernatant was determined in MDCK cells.
[†]Unless otherwise indicated, plasmids were constructed with cDNAs representing the RNAs of A/WSN/33 virus.

Efficiency of Influenza Virus Production with Coexpression of all Viral Structural Proteins.

Although expression of the viral NP and polymerase proteins is sufficient for the plasmid-driven generation of influenza viruses, it was possible that the efficiency could be improved. In previous studies, the expression of all influenza virus structural proteins (PB2, PB1, PA, HA, NP, NA, M1, M2, and NS2) resulted in VLPs that contained an artificial vRNA encoding a reporter chloramphenicol-acetyltransferase gene (Mena et al., 1996). Thus, the availability of the entire complement of structural proteins, instead of only those required for viral RNA replication and transcription, might improve the efficiency of virus production. To this end, 293T cells were transfected with optimal amounts of viral protein expression plasmids (as judged by VLP production; unpublished data): 1 µg of pcDNA762(PB2) and pcDNA774 (PB1); 0.1 µg of pcDNA787(PA); 1 µg of pEWSN-HA, pCAGGS-WSN-NP0/14, and pCAGGS-WNA15; 2 µg of pCAGGS-WSN-M1-2/1; 0.3 µg of pCA-NS2; and 0.03 µg of pEP24c (for M2), together with 1 µg of each RNA polymerase I plasmid (Experiment 2, Table 1). A second set of cells was transfected with the same set of RNA polymerase I plasmids, with the exception of the PB1 gene, for which pPolI-PR/8/34-PB1 was substituted in an effort to generate a reassortant virus, together with plasmids expressing only PA, PB1, PB2, and NP (Experiment 3, Table 1) or those expressing all the influenza structural proteins (Experiment 4, Table 1). Yields of WSN virus did not appreciably differ at 24 hours (Experiments 1 and 2, Table 1) or at 36 hours (data not shown) post-transfection. However, more than a 10-fold increase in yields of the virus with PR/8/34-PB1 was found when all the influenza viral structural proteins were provided (Experiments 3 and 4, Table 1). Negative controls, which lacked one of the plasmids for the expression of PA, PB1, PB2, of NP proteins, did not yield any virus (Experiments 5-8, Table 1). Thus, depending on the virus generated, expression of all influenza A virus structural proteins appreciably improved the efficiency of the reverse genetics method.

Next, the kinetics of virus production after transfection of cells was determined using the set of plasmids used to generate a virus with the A/PR/8/34-PB1 gene. In two of three experiments, virus was first detected at 24 hours after transfection. The titer measured at that time, $>10^3$ pfu/ml, had increased to $>10^6$ pfu/ml by 48 hours after transfection (Table 2). To estimate the percentage of plasmid-transfected cells that were producing viruses, 293T cells were treated with EDTA (0.02%) at 24 hours after transfection to disperse the cells, and then performed limiting dilution studies. In this experiment, no free virus was found in the culture supernatant at this time point. The results indicated that 1 in $10^{3.3}$ cells was generating infectious virus particles.

TABLE 2

Kinetics of virus production after plasmid transfection into 293T cells*

| Hours after plasmid transfection | Virus titers in culture supernatant (pfu/ml) Experiment | | |
|---|---|---|---|
| | 1 | 2 | 3 |
| 6 | 0 | ND | ND |
| 12 | 0 | ND | 0 |
| 18 | 0 | ND | 0 |
| 24 | 0 | $2 \times 10^3$ | $6 \times 10^3$ |
| 30 | ND | $5 \times 10^4$ | $9 \times 10^4$ |
| 36 | $6 \times 10^2$ | $>1 \times 10^5$ | $7 \times 10^5$ |
| 42 | ND | $>1 \times 10^6$ | $5 \times 10^6$ |
| 48 | $8 \times 10^4$ | $>1 \times 10^6$ | $1 \times 10^7$ |

*293T cells were transfected with eight RNA polymerase I plasmids encoding A/WSN/33 virus genes with the exception of PB1 gene, which is derived from A/PR/8/34 virus, and nine protein expression plasmids as described in the text. At different time points, we titrated virus in the culture supernatant in MDCK cells.
ND = not done.

Recovery of Influenza Virus Containing the FLAG Epitope in the NA Protein.

Figure 4:
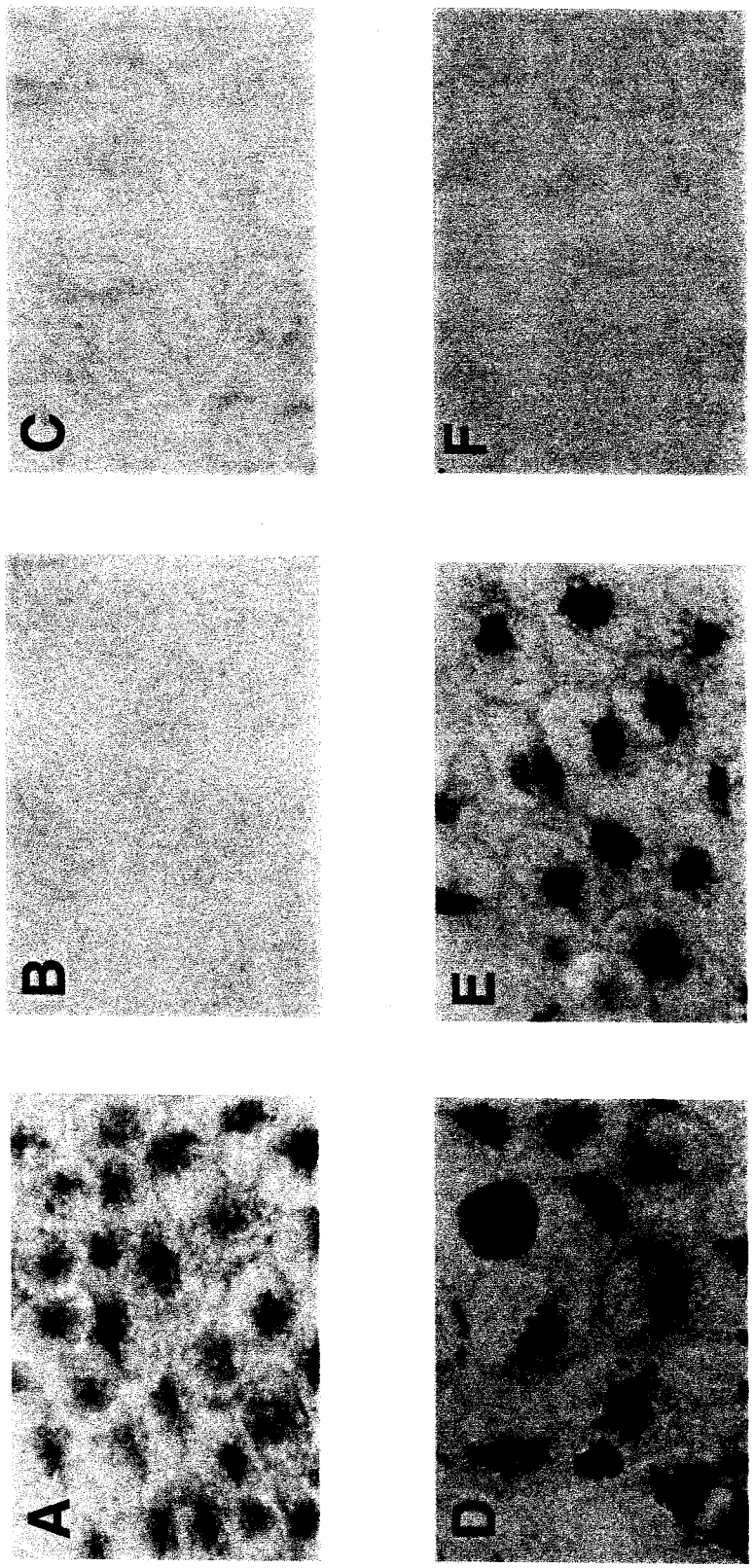
FIG. 4. Detection of the FLAG epitope in cells infected with a transfectant virus. Antibody staining was used to identify the NA in MDCK cells infected with either PR8-WSN-FL79 (A, D) or A/WSN/33 wild-type virus (B, E), or on mock-infected MDCK cells (C, F). Nine hours after infection, cells were fixed with paraformaldehyde, treated with Triton X-100 and incubated with either anti-FLAG (A-C) or anti-WSN NA (D-F) monoclonal antibodies. Intensive Golgi staining (red) is apparent in positive samples (A, D, and E).

To verify that the new reverse genetics system allowed the introduction of mutations into the genome of influenza A viruses, a virus containing a FLAG epitope (Castrucci et al., 1992) in the NA protein was generated. 293T cells were transfected with an RNA polymerase I plasmid (pPolI-WSN-NA/FL79) that contained a cDNA encoding both the NA protein and a FLAG epitope at the bottom of the protein's head, together with the required RNA polymerase I and protein expression plasmids. To confirm that the recovered virus (PR8-WSN-FL79) did in fact express the NA-FLAG protein, immunostaining assays of cells infected with PR8-WSN-FL79 or A/WSN/33 wild-type virus was performed. A monoclonal antibody to the FLAG epitope detected cells infected with PR8-WSN-FL79, but not those infected with wild-type virus (FIG. 4). Recovery of the PR8-WSN-FL79 virus was as efficient as that for the untagged wild-type virus (data not shown). These results indicate that the new reverse genetics system allows one to introduce mutations into the influenza A virus genome.

Generation of Infectious Influenza Virus Containing Mutations in the PA Gene.

Figure 5:
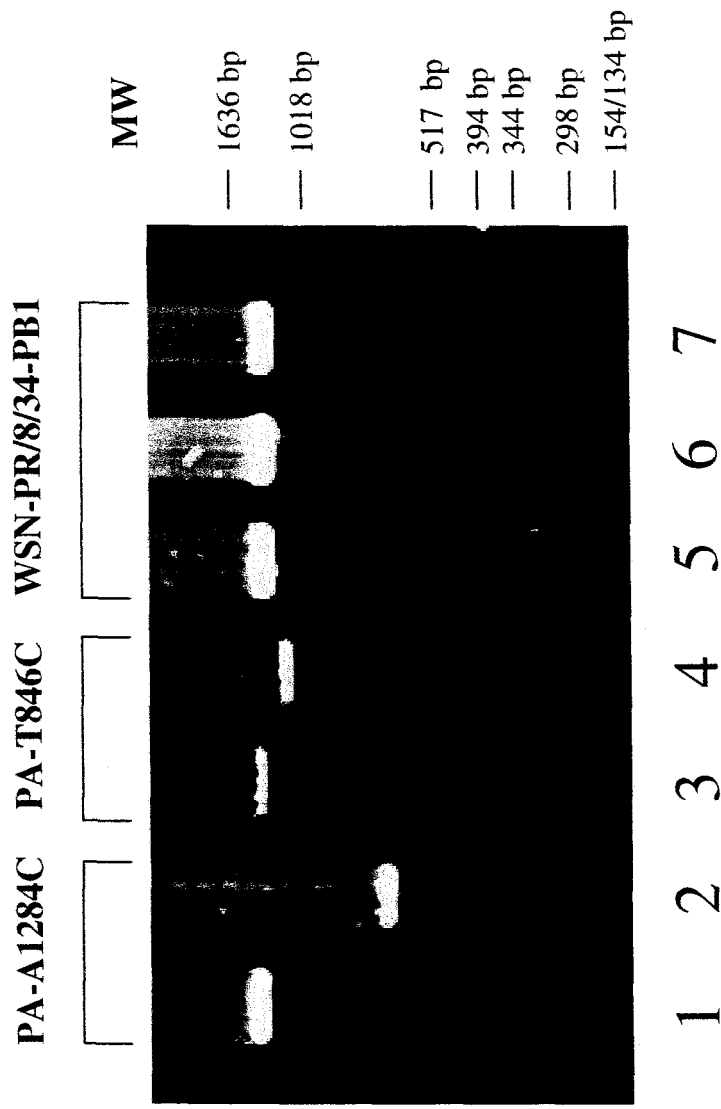
FIG. 5. Recovery of PA mutants. The PA gene of each virus was amplified by RT-PCR with primers that yield a 1226 bp fragment (position 677 to 1903 of the mRNA, lanes 1, 3, 5), which was then digested with the restriction enzyme Bsp120I (at position 846 of the mRNA, lanes 4, 7) or PvuII (at position 1284 of the mRNA, lanes 2, 6). The presence of Bsp120I or PvuII sites in the PCR products yielded either 169 bp and 1057 bp or 607 bp and 619 bp fragments, respectively. MW=molecular weight markers.

To produce viruses possessing mutations in the PA gene, two silent mutations were introduced creating new recognition sequences for restriction endonucleases (Bsp120I at position 846 and PvuII at position 1284 of the mRNA). Previously, it was not possible to modify this gene by reverse genetics, because of the lack of a reliable selection system. Transfectant viruses, PA-T846C and PA-A1284 were recovered. The recovered transfectant viruses were biologically cloned by two consecutive limiting dilutions. To verify that the recovered viruses were indeed transfectants with mutations in the PA gene, cDNA for the PA gene was obtained by reverse transcriptase-PCR. As shown in FIG. 5, PA-T846C and PA-A1284C viruses had the expected mutations within the PA gene, as demonstrated by the presence of the newly introduced restriction sites. PCR of the same viral samples and primers without the reverse transcription step failed to produce any products (data not shown), indicating that the PA cDNA was indeed originated from vRNA instead of the plasmid used to generate the viruses. These results illustrate how viruses with mutated genes can be produced and recovered without the use of helper viruses.

Discussion

The reverse genetics systems described herein allows one to efficiently produce influenza A viruses entirely from cloned cDNAs. Bridgen and Elliott (1996) also used reverse genetics to generate a Bunyamwera virus (Bunyaviridae family), but it contains only three segments of negative-sense RNA, and the efficiency of its production was low, $10^2$ pfu/$10^7$ cells. Although the virus yields differed among the experiments, consistently $>10^3$ pfu/$10^6$ cells was observed for influenza virus, which contains eight segments. There are several explanations for the high efficiency of the reverse genetics system described hereinabove. Instead of producing RNPs in vitro (Luytjes et al., 1989), RNPs were generated in vivo through intracellular synthesis of vRNAs using RNA polymerase I and through plasmid-driven expression of the viral polymerase proteins and NP. Also, the use of 293T cells, which are readily transfected with plasmids (Goto et al., 1997), ensured that a large population of cells received all of the plasmids needed for virus production. In addition, the large number of transcripts produced by RNA polymerase I, which is among the most abundantly expressed enzymes in growing cells, likely contributed to the overall efficiency of the system. These features led to a correspondingly abundant number of vRNA transcripts and adequate amounts of viral protein for encapsidation of vRNA, formation of RNPs in the nucleus, and export of these complexes to the cell membrane, where new viruses are assembled and released.

Previously established reverse genetics systems (Enami et al., 1990; Neumann et al., 1994; Luytjes et al., 1989; Pleschka et al., 1996) require helper-virus infection and therefore selection methods that permit a small number of transfectants to be retrieved from a vast number of helper viruses. Such strategies have been employed to generate influenza viruses that possess one of the following cDNA-derived genes: PB2 (Subbarao et al., 1993), HA (Enami et al., 1991: Horimoto et al., 1994), NP (Li et al., 1995), NA (Enami et al., 1990), M (Castrucci et al., 1995; Yasuda et al., 1994), and NS (Enami et al., 1991). Most of the selection methods, except for those applicable to the HA and NA genes, rely on growth temperature, host range restriction, or drug sensitivity, thus limiting the utility of reverse genetics for functional analysis of the gene products. Even with the HA and NA genes, for which reliable antibody-driven selection systems are available, it is difficult to produce viruses with prominent growth defects. In contrast, the reverse genetics system described herein does not require helper virus and permits one to generate transfectants with mutations in any gene segment or with severe growth defects. This advantage is demonstrated in FIG. 5, which the recovery of transfectant viruses with a mutated PA gene. Having the technology to introduce any viable mutation into the influenza A virus genome will enable investigators to address a number of long-standing issues, such as the nature of regulatory sequences in nontranslated regions of the viral genome, structure-function relationships of viral proteins, and the molecular basis of host-range restriction and viral pathogenicity.

Although inactivated influenza vaccines are available, their efficacy is suboptimal due partly to their limited ability to elicit local IgA and cytotoxic T cell responses. Clinical trials of cold-adapted live influenza vaccines now underway suggest that such vaccines are optimally attenuated, so that they will not cause influenza symptoms, but will still induce protective immunity (reviewed in Keitel & Piedra, 1998). However, preliminary results indicate that these live virus vaccines will not be significantly more effective than the best inactivated vaccine (reviewed in Keitel. & Piedra, 1998), leaving room for further improvement. One possibility would be to modify a cold-adapted vaccine with the reverse genetics system described above. Alternatively, one could start from scratch by using reverse genetics to produce a "master" influenza A strain with multiple attenuating mutations in the genes that encode internal proteins. The most intriguing application of the reverse genetics system described herein may lie in the rapid production of attenuated live-virus vaccines in cases of suspected pandemics involving new HA or NA subtypes of influenza virus.

This new reverse genetics system will likely enhance the use of influenza viruses as vaccine vectors. The viruses can be engineered to express foreign proteins or immunogenic epitopes in addition to the influenza viral proteins. One could, for example, generate viruses with foreign proteins as a ninth segment (Enami et al., 1991) and use them as live vaccines. Not only do influenza viruses stimulate strong cell-mediated and humoral immune responses, but they also afford a wide array of virion surface HA and NA proteins (e.g., 15 HA and 9 NA subtypes and their epidemic variants), allowing repeated immunization of the same target population.

Influenza VLPs possessing an artificial vRNA encoding a reporter gene have been produced by expressing viral structural proteins and vRNA with the vaccinia-T7 polymerase system (Mena et al., 1996). Using reverse genetics, one can now generate VLPs containing vRNAs that encode proteins required for vRNA transcription and replication (i.e., PA, PB1, PB2, and NP), as well as vRNAs encoding proteins of interest. Such VLPs could be useful gene delivery vehicles. Importantly, their lack of genes encoding viral structural proteins would ensure that infectious viruses will not be produced after VLP-gene therapy. Since the influenza virus genome is not integrated into host chromosome, the VLP system would be suitable for gene therapy in situations requiring only short-term transduction of cells (e.g., for cancer treatment). In contrast to adenovirus vectors (Kovesdi et al., 1997), influenza VLPs could contain both HA and NA variants, allowing repeated treatment of target populations.

The family Orthomyxoviridae comprises influenza A, B, and C viruses, as well as the recently classified Thogotovirus. The strategy for generating infectious influenza A viruses entirely from cloned cDNAs described herein would apply to any orthomyxovirus, and perhaps to other segmented negative-sense RNA viruses as well (e.g., Bunyaviridae, Arenaviridae). The ability to manipulate the viral genome without technical limitations has profound implications for the study of viral life cycles and their regulation, the function of viral proteins and the molecular mechanisms of viral pathogenicity.

Example 2

Figure 7:
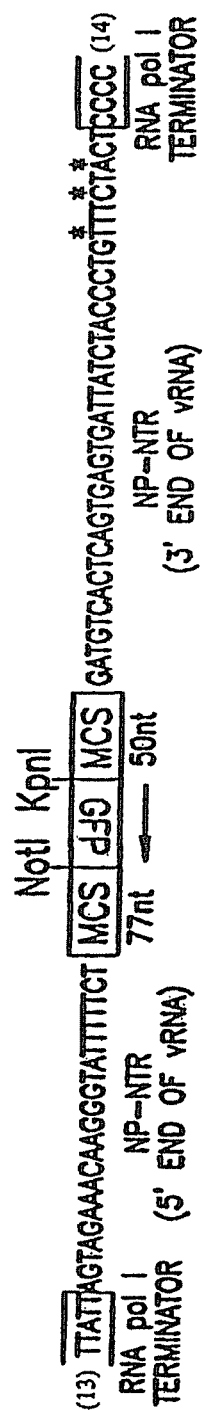
FIG. 7. The pPolI-GFP plasmid for generating influenza virus-like RNA encoding the GFP protein. This plasmid contains the GFP gene (derived from pEGFP-N1; Clontech, Palo Alto, Calif.) in antisense orientation between the 5' and 3' noncoding regions of influenza A virus segment 5, flanked by the human RNA polymerase I promoter and the mouse RNA polymerase I terminator. The numeric number in a parenthesis positioned next to a nucleotide sequence represents the SEQ ID NO for that sequence.
Figure 8:
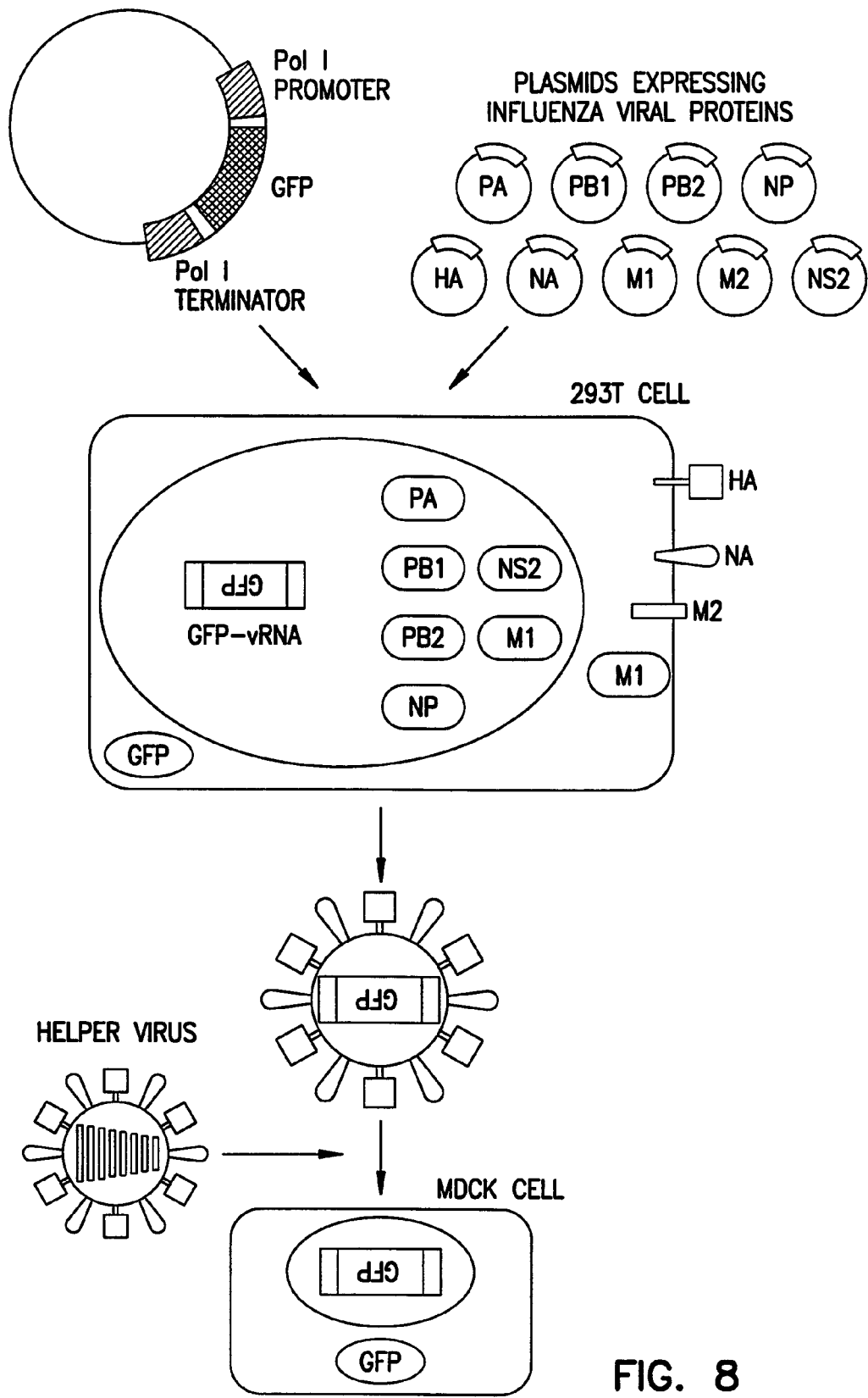
FIG. 8. Schematic diagram of VLP generation strategy. Individual protein expression plasmids and a plasmid containing the RNA polymerase I promoter, a cDNA encoding the GFP reporter gene, and the RNA polymerase I terminator are transfected into 293T cells. Intracellular transcription by RNA polymerase I yields GFP vRNA of negative polarity, as indicated by inverted letters. Supernatants containing VLPs are harvested, mixed with influenza helper virus and inoculated into MDCK cells.

Expression of the Influenza Virus Proteins PB2, PB1, PA, and NP Leads to Replication and Transcription of an Artificial Viral RNA To generate influenza VLPs, the RNA polymerase I system for the intracellular synthesis of influenza viral RNAs in vivo was employed (FIG. 7). In this system, a cDNA encoding a reporter gene in antisense orientation is flanked by the 5' and 3' noncoding regions of an influenza viral RNA. This cassette is inserted between an RNA polymerase I promoter and terminator. Transfection of such constructs into eukaryotic cells leads to transcription of the reporter gene by cellular RNA polymerase I, thereby generating influenza virus-like RNAs (Neumann et al., 1994). Upon influenza virus infection, the artificial vRNAs are replicated and transcribed by the viral polymerase complex, resulting in the expression of the reporter gene.

Figure 9A:
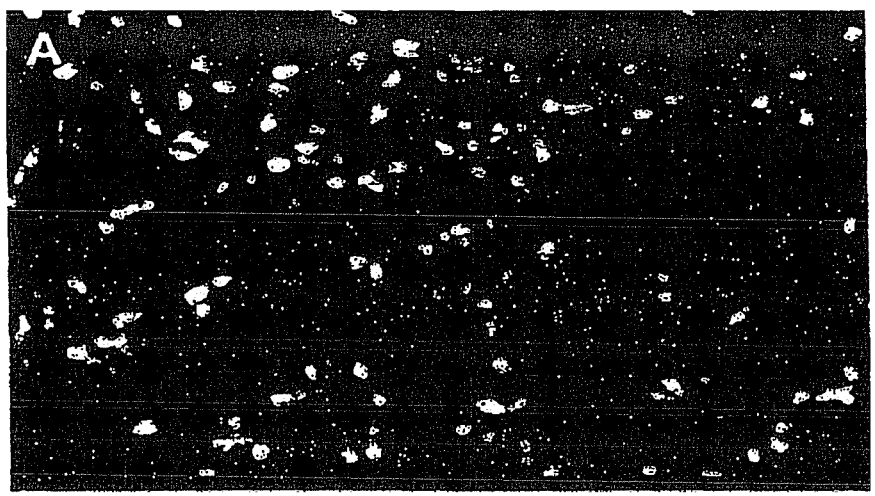
FIG. 9. The PA, PB1, PB2, and NP proteins of influenza A virus encapsidate GFP vRNA produced by RNA polymerase I, leading to GFP expression. 293T cells were transfected with plasmids expressing the PB2, PB1, PA and NP proteins (A) or with all plasmids except the one expressing the NP protein (B), together with the RNA polymerase I-GFP gene plasmid for intracellular synthesis of reporter gene vRNA. Cells were fixed 48 h after transfection, and GFP expression was determined with a fluorescence microscope.
Figure 9B:
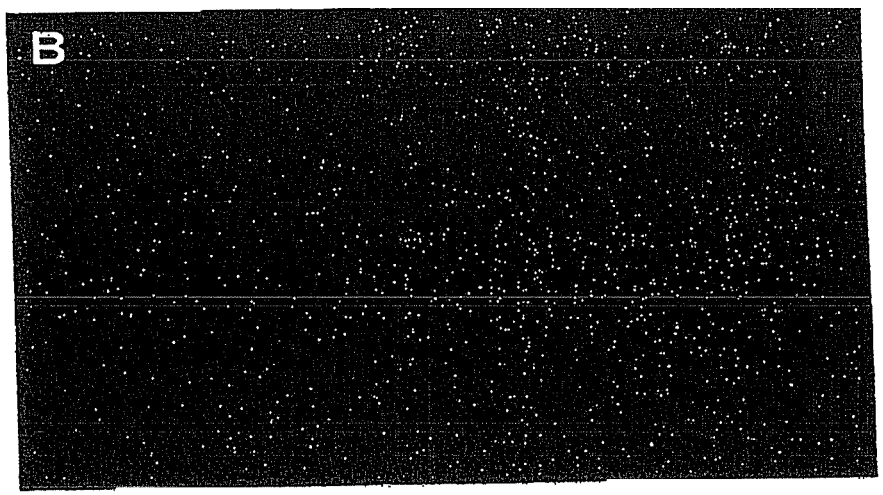

To determine whether expression of the PB2, PB1, PA, and NP proteins leads to expression of the reporter gene encoded by the RNA polymerase I-derived transcript, plasmids (1 µg each) expressing the NP protein of A/WSN/33 (H1N1) virus under control of the chicken β-actin promoter (pCAGGS-WSN-NP0/14), the polymerase proteins of A/PR/8/34 virus under control of the cytomegalovirus promoter [pcDNA762 (PB2), pcDNA774(PB1), and pcDNA787(PA)], and an RNA polymerase I reporter gene construct (pPolI-GFP) were transfected into human embryonic kidney (293T) cells. Forty eight hours later, 30%-40% of the cells were expressing GFP (FIG. 9). In contrast, GFP expression could not be detected in transfected cells lacking the polymerase or NP proteins. These results indicated that NP and the three influenza viral polymerase proteins had formed a functional complex that replicated and transcribed the RNA polymerase I-derived GFP vRNA.

Optimal vRNA Transcription and Replication.

To determine the amounts of plasmid DNA required for optimal reporter GFP expression, we modulated the expression of the polymerase proteins and NP. Previous studies had indicated that large amounts of PA reduce the extent of reporter gene expression in transcription/replication systems (Mena et al., 1996). Therefore, in a stepwise manner, the expression of PA from the plasmid was reduced, identifying 0.1 µg of pcDNA787(PA) as the template amount yielding the strongest expression of GFP. With NP, the major structural component of RNP complexes, high amounts of protein expression plasmid may be required. However, higher amounts of the plasmid did not appreciably affect the number of GFP-positive 293T cells. In addition, various amounts of the PB2 and PB1 protein expression plasmids (ranging from 1.0 to 0.03 µg) did not affect the GFP expression in 293T cells. Hence, in all subsequent experiments, 0.1 µg of pcDNA787(PA), and 1.0 µg of pcDNA774(PB1), pcDNA762 (PB2), and pCAGGS-WSN-NP0/14, was used.

Formation of Influenza VLPs from Cloned cDNAs.

Previous studies with the vaccinia virus T7 RNA polymerase system showed that the formation of influenza VLPs requires nine influenza virus proteins: PB2, PB1, PA, HA, NA, NP, M1, M2, and NS2 (Mena et al., 1996). The NS1 protein, by contrast, is dispensable for particle formation (Mena et al., 1996). To establish an efficient plasmid-driven system for VLP generation, cDNAs were generated that encoded the HA, NA, M1, M2, and NS2 genes. The cDNAs were cloned into the eukaryotic expression vector pCAGGS/MCS (controlled by the chicken β-actin promoter), resulting in pEWSN-HA, pCAGGS-WNA15, pCAGGS-WSN-M1-2/1, pEP24c, and pCA-NS2, respectively. Expression of each protein was confirmed by Western blot analysis.

To generate VLPs, $10^6$ 293T cells were transfected with 1.0 µg of each protein expression plasmids (with the exception of pcDNA787(PA), for which 0.1 µg was employed), and with 1 µg of the reporter gene construct pPolI-GFP. Culture supernatants were harvested 48 hours after transfection and mixed with A/WSN/33 virus to provide the influenza virus proteins required for replication and transcription of GFP vRNA. The mixture was then inoculated into MDCK cells. Ten hours after incubation, GFP-positive MDCK cells were detected, corresponding to 450 particles/ml of supernatant (Table 3). Thus, plasmid-driven expression of all influenza viral structural proteins resulted in the formation of infectious influenza VLPs containing GFP vRNA. Moreover, GFP vRNA was delivered to MDCK cells.

Optimal Assembly of Influenza Virus.

VLP formation was also studied in cells expressing different amounts of the RNA polymerase I reporter gene construct, as well as HA, NA, M1, M2, and NS2 plasmid DNAs. In experiments with pPolI-GFP, 1.0 µg of the plasmid DNA was highly efficient in generating VLPs, whereas the efficiency was significantly reduced for 2.0 µg or 3.0 µg. Because the NS2 and M2 proteins are expressed in low amounts late in infection, it was likely that relatively small amounts of the expression plasmids would be needed for optimal VLP formation. Reduction of the M2 expression construct from 1.0 µg to 0.3 µg resulted in a more than tenfold increase in the number of GFP-positive MDCK cells (Table 3). Further reduction of plasmid to 0.03 µg did not increase the number of VLPs. For NS2, lower amounts of plasmid tested (0.1 µg) were associated with less efficient formation of VLPs (Table 3).

Figure 10A:
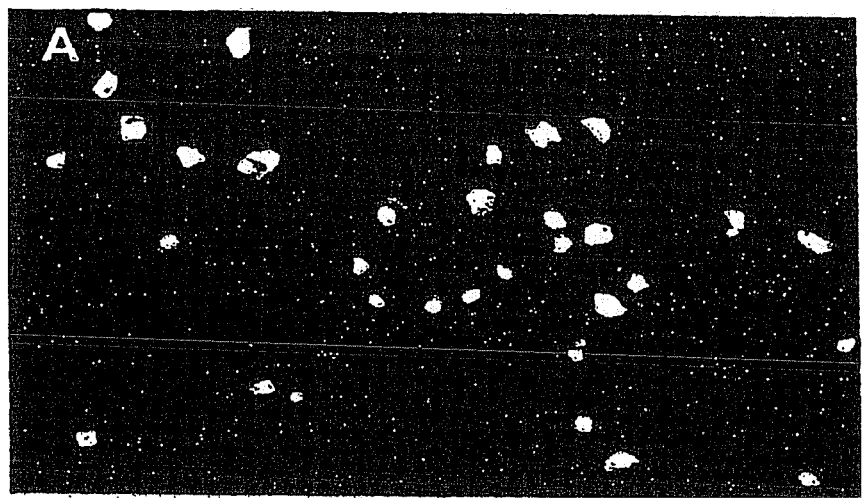
FIG. 10. Generation of infectious influenza VLPs. 293T cells were transfected with nine plasmids, each expressing a different viral structural protein (A), or with eight plasmids omitting the construct for NP (B), together with the RNA polymerase I-GFP gene plasmid. Forty-eight hours after transfection, VLP-containing supernatants were collected, mixed with A/WSN/33 helper virus, and inoculated into MDCK cells. Cells were fixed at 10 hours after infection, and GFP expression was determined with a fluorescence microscope.
Figure 10B:
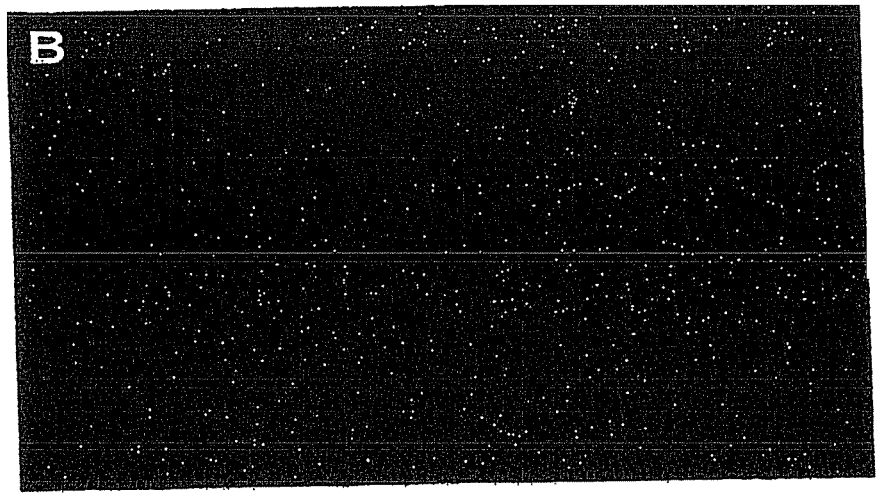

The M1 protein is the major structural component of the virion. Thus, high levels of M1 expression are likely required for efficient formation of VLPs. This prediction was tested in experiments comparing VLP formation in cells transfected with 1.0 µg or 2.0 µg of M1 plasmid DNA. As shown in Table 3, higher amounts of plasmid resulted in a more than tenfold increase in the number of GFP-positive MDCK cells. Comparison of two different amounts (1 g vs. 2 µg) of plasmids expressing the HA and NA proteins did not reveal any appreciable differences in VLP formation, leading to selection of 1 µg of each plasmid (pEWSN-HA, pCAGGS-WNA15) for use in subsequent experiments. Overall, these studies resulted in a >100-fold increase in the efficiency of VLP formation, ultimately leading to the production of more than $10^4$ infectious influenza virus particles per ml of supernatant (FIG. 10).

TABLE 3

Optimal amounts of plasmid DNA for the formation of infectious VLPs.*

| Amount (µg) of plasmid DNA expressing: | | | | | | | | | GFP vRNA | Relative efficiency of VLP formation[†] |
|---|---|---|---|---|---|---|---|---|---|---|
| PB2 | PB1 | PA | HA | NP | NA | M1 | M2 | NS2 | | |
| 1.0 | 1.0 | 0.1 | 1.0 | 1.0 | 1.0 | 1.0 | 1.0 | 1.0 | 1.0 | 1 |
| 1.0 | 1.0 | 0.1 | 1.0 | 1.0 | 1.0 | 1.0 | 0.1 | 1.0 | 1.0 | 28 |

TABLE 3-continued

Optimal amounts of plasmid DNA for the formation of infectious VLPs.*

Amount (μg) of plasmid DNA expressing:

| PB2 | PB1 | PA | HA | NP | NA | M1 | M2 | NS2 | GFP vRNA | Relative efficiency of VLP formation[†] |
|---|---|---|---|---|---|---|---|---|---|---|
| 1.0 | 1.0 | 0.1 | 1.0 | 1.0 | 1.0 | 1.0 | 0.03 | 1.0 | 1.0 | 17 |
| 1.0 | 1.0 | 0.1 | 1.0 | 1.0 | 1.0 | 1.0 | 0.1 | 1.0 | 1.0 | 28 |
| 1.0 | 1.0 | 0.1 | 1.0 | 1.0 | 1.0 | 1.0 | 0.1 | 0.3 | 1.0 | 24 |
| 1.0 | 1.0 | 0.1 | 1.0 | 1.0 | 1.0 | 1.0 | 0.1 | 0.1 | 1.0 | 11 |
| 1.0 | 1.0 | 0.1 | 1.0 | 1.0 | 1.0 | 1.0 | 0.1 | 1.0 | 1.0 | 28 |
| 1.0 | 1.0 | 0.1 | 1.0 | 1.0 | 1.0 | 2.0 | 0.1 | 1.0 | 1.0 | 220 |

*293T cells were transfected with expression plasmids for all nine influenza virus structural proteins and with the RNA polymerase I-GFP gene plasmid. Forty-eight hours after transfection, VLP-containing supernatants were collected, mixed with A/WSN/33 helper virus, and inoculated into MDCK cells. The cells were fixed 10 h after infection and GFP expression was determined with a fluorescence microscope. Only the amounts of the M1, M2, and NS2 plasmids were varied (bold letter) to determine their optimal amounts for GFP expression in MDCK cells.
[†]The relative efficiency of VLP formation was determined by counting the number of GFP-positive cells in five microscopic fields. The sample containing 1 μg of each plasmid (which yielded 450 infectious VLP/ml of supernatant) was chosen as the reference (value of 1).

Authenticity of VLPs Produced Entirely from Plasmids.

To verify that VLPs initiate infection in the same manner as authentic influenza viruses, VLPs were neutralized with antibody to the WSN HA. VPL-containing supernatants derived from plasmid-transfected 293T cells were incubated with a pool of anti-WSN HA monoclonal antibodies or with a monoclonal antibody to the G protein of vesicular stomatitis virus (VSV) (negative control) for 1 hour at room temperature. A/PR/8/34 helper virus, which is not neutralized by the pool of anti-WSN HA monoclonal antibodies, was added to the mixture and inoculated into MDCK cells. Only the anti-WSN-HA-specific monoclonal antibody neutralized the VLPs, indicating that the HA medicates the attachment and entry of VLPs into cells.

Next, the minimal set of proteins required for the formation of VLPs was identified. Other have established that the three influenza virus polymerases and the NP are essential for the replication and transcription of vRNA (Honda et al., 1988). Therefore, each of these four proteins was included, but HA, NA, M1, M2, or NS2 was consecutively omitted. Exclusion of any of these plasmids did not affect the replication/transcription of GFP vRNA in transfected 293T cells. Supernatants derived from transfected 293T cells that lacked the HA, NA, M1, or NS2 protein did not promote GFP expression in infected MDCK cells, indicating the absence of infectious VLPs. Infectious VLPs were detected with omission of M2 but the number was low (>500 fold reduction compared to the full set of structural proteins). Thus, all influenza virus structural proteins are required for the efficient formation of infectious VLPs, in accord with data from studies of the vaccinia-virus system (Mena et al., 1996).

VSV Glycoprotein can Replace the HA and NA Proteins in the Production of VLPs.

The influenza virus HA and NA proteins were replaced with the VSV G protein, which functions in receptor binding and fusion. In 293T cells transfected with pPolI-GFP; optimal amounts of the PB2, PB1, PA, NP, M1, M2, and NS2 expression constructs; and 1 μg of the VSV-G construct (pCAGGS-VSV-G), substitution of the VSV-G protein for influenza virus glycoproteins did not adversely affect VLP formation. To the contrary, higher numbers of GFP-positive cells were reproducibly found when VSV-G, rather than the HA and NA, served as the viral glycoprotein. Thus, the VSV G protein can be efficiently incorporated into influenza virions and can function as well as the HA and NA in virus release and entry.

An efficient system for generating infectious influenza virus particles would be an asset in research with this virus and potentially in the production of vaccines and vectors for gene therapy. In contrast to the extant vaccinia virus system, the VLP production strategy described here is highly efficient, both in the initial transfection of cells and in the yield of VLPs (>$10^4$ infectious particles/ml of supernatant). Moreover, it is driven entirely by plasmids expressing influenza virus proteins (i.e., in the absence of any other viral proteins), which greatly simplifies the interpretation of results. Another major advantage is the capability to study the effects of lethal mutations in virion formation, packaging of RNP complexes, budding of virus replication, and binding and fusion processes. In addition, it is likely that the system described hereinabove would operate equally well with other viruses, e.g., paramyxoviruses and rhabdoviruses.

Influenza virus HA and NA proteins can be functionally replaced by the VSV glycoprotein G. Previously, it had been reported that influenza viruses failed to incorporate VSV G protein when provided by recombinant SV40 virus (Naim et al., 1993). The results described herein suggest that neither the HA nor the NA is essential for the formation of VLPs, although it cannot be ruled out that these glycoproteins play a role in interactions with other viral proteins, thus affecting the structure of virions, as suggested by the elongated shapes of viruses expressing tail-less HAs, NAs, or both (Garcia-Sastre et al., 1995; Jin et al., 1994; Jin et al., 1997; Mitnaul et al., 1996).

The plasmid-based system described hereinabove may be particularly useful for therapeutic gene delivery. VLPs can be prepared that contain the vRNA encoding the proteins required for transcription and replication (i.e., the NP and the polymerases), as well as a vRNA encoding the protein of interest. These particles are infectious and can deliver a designated gene into target cells, where it would replicate and be transcribed. Because these particles do not contain a complete complement of viral genes, they can not produce infectious progeny viruses. This feature, together with the lack of integration of the viral genome into host chromosomes, would ensure the biological safety of gene delivery in human and nonhuman subjects. Finally, the availability of 15 HA and 9 NA subtypes and their variants would allow the repeated administration of VLPs, thereby overcoming immunoresistance to vector-generated proteins, one of the major obstacles faced with repeated use of other viral vectors, such as adenoviruses. A further benefit of the plasmid-driven system would be realized in situations requiring only short-term expression of foreign proteins, as in cancer treatment.

Example 3

Figure 11:
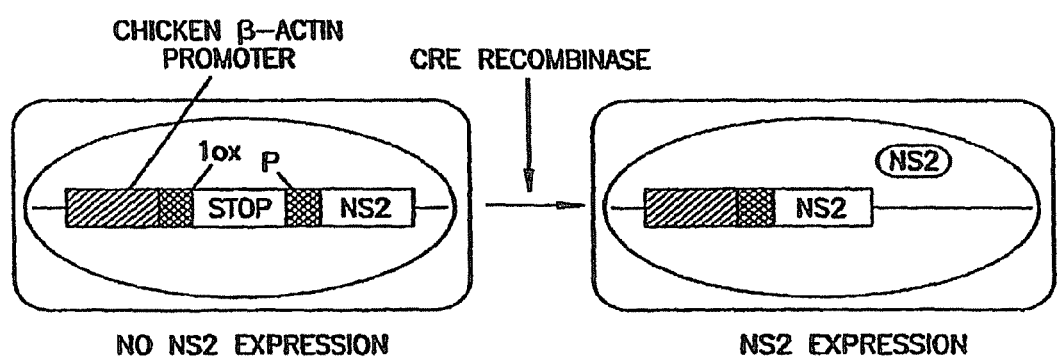
FIG. 11. Schematic of the use of Cre recombinase to express influenza NS2 protein in a cell, the genome of which is augmented with a recombinant DNA molecule. The genome of the cell comprises a recombinant DNA molecule which comprises a promoter linked to a site specific recombination site (e.g., loxP) linked to a transcription stop sequence linked to a second site specific recombination site in the same orientation as the first site specific recombination site linked to the NS2 gene.
Figure 12:
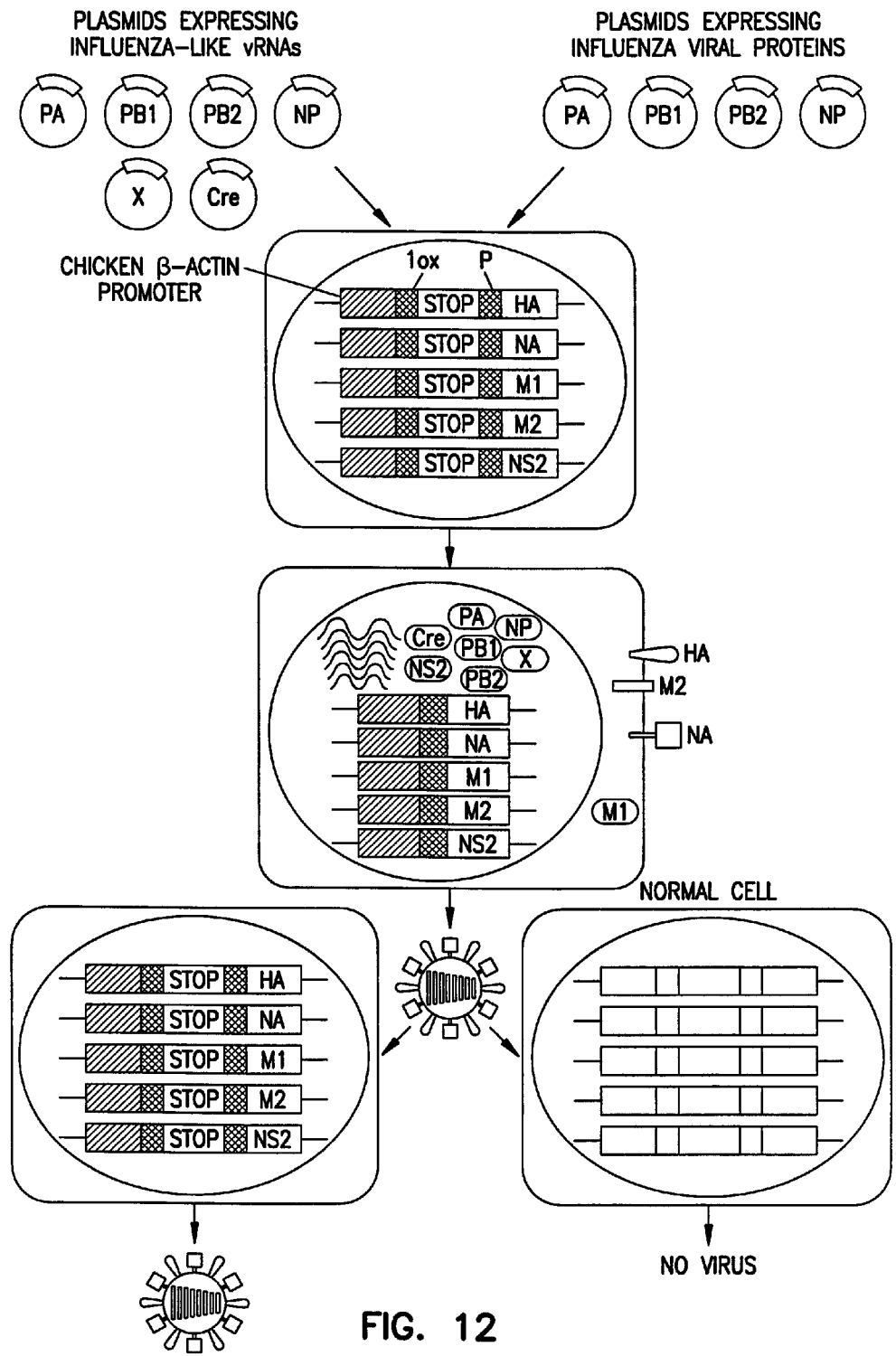
FIG. 12. Preparation of replication defective influenza virus.

By using the Cre-loxP system, one can generate packaging cell lines for the production of replication-defective viruses. For example, a protein expression vector is prepared that contains a transcription stop cassette (e.g., pBS302 of Life Technologies, Bethesda, Md.; and Sauer et al., 1993; Lasko et al., 1992; Pichel et al., 1993; Bolivar et al., 1977; Stuhl et al., 1981; Stuhl, 1985; Fiers et al., 1978), flanked by two loxP sites, and one of the viral genes. Transcription, initiated at the promoter sequence, is blocked at the transcription stop sites. Thus, the viral gene is not transcribed and translated. A cell that is stably transfected with such a vector is infected with an influenza virus that lacks the vRNA encoding the gene cloned into the loxP system. This virus also contains an additional vRNA encoding the Cre protein. This virus is not viable in normal cells, because it lacks one of its vRNAs. However, in the packaging cell line, the Cre protein which is expressed from the vRNA results in recombination at the loxP site, resulting in the deletion of the transcription stop site. Thus, the respective viral gene(s) is now transcribed and expressed, allowing the virus to amplify in these cells (FIG. 11).

In addition, packaging cell lines are prepared that express the late viral proteins (i.e., HA, NA, M1, M2, and NS2) controlled by the loxP system (FIG. 12). The HA and NA can be replaced by other viral receptor-binding and fusion proteins (e.g., Ebola GP, Marburg GP, Bunyaviridae glycoproteins GP1 and GP2, the G and/or F proteins of rhabdovirus and paramyxovirus, thogotovirus glycoprotein, and the glycoproteins of positive-strand RNA viruses). Virus-like particles are generated which contain the vRNAs encoding the proteins required for replication/transcription (i.e., the polymerase and NP proteins), a vRNA encoding the gene of interest, and a vRNA encoding Cre. These vRNAs are packaged into virus-like particles in the packaging cell lines.

These virus-like particles can be used for vaccine and gene therapy purposes because (i) they do not contain the full complement of viral genes and thus no infectious progeny particles can be formed, meeting the stringent safety concerns; (ii) they will likely express the foreign protein at high levels; (iii) they do not express the viral glycoproteins (HA, NA) that are the major antigens; thus, the host immune response against the viral proteins should be limited.

REFERENCES

Albo, C., Martin, J., and Portela, A. *J. Virol.,* 70, 9013-9017 (1996).
Baron, M. D. & Barrett, T. *J. Virol.,* 71, 1265-1271 (1997).
Bolivar et al. *Gene*, 2, 95 (1977).
Bridgen, A. & Elliott, R. M. *Proc. Natl. Acad. Sci. U.S.A.,* 93, 15400-15404 (1996).
Castrucci, M. R. & Kawaoka, Y. *J. Virol.,* 69, 2725-2728 (1995).
Castrucci, M. R., Bilsel, P. & Kawaoka, Y. *J. Virol.,* 66, 4647-4653 (1992).
Collins, P. L., Hill, M. G., Camargo, E., Grosfeld, H., Chanock, R. M. & Murphy, B. R. *Proc. Natl. Acad. Sci. U.S.A.,* 92, 11563-11567 (1995).
Cozelmann, K. K. & Schnell, M. *J. Virol.,* 68, 713-719 (1994).
Dunn, E. F., Pritlove, D. C., Jin, H., and Elliott, R. M. *Virology,* 211, 133-143 (1995).
Elliott, R. M. *Mol. Med.,* 3, 572-577 (1997.
Enami, M., Sharma, G., Benham, C. & Palese, P. *Virology,* 185, 291-298 (1991).
Enami, M. & Palese, P. *J. Virol.,* 65, 2711-2713 (1991).
Enami, M., Luytjes, W., Krystal, M. & Palese, P. *Proc. Natl. Acad. Sci. U.S.A.,* 87, 3802-3805 (1990).
Fiers et al. *Nature,* 273, 113 (1978).
Garcia-Sastre, A. And P. Palese. *Virus Res.,* 37, 37-47 (1995).
Garcin, D., Pelet, T., Calain, P., Roux, L., Curran, J. & Kolakofsky, D. *EMBO J.,* 14, 6087-6094 (1995).
Goto, H., Bethell, R. C. & Kawaoka, Y. *Virology,* 238, 265-272 (1997).
Hagen, M., Chung, T. D. Y., Butcher, J. A., and Krystal, M. *J. Virol.,* 68, 1509-1515 (1994).
He, B., Paterson, R. G., Ward, C. D. & Lamb, R. A. *Virology,* 237, 249-260 (1997).
Hoffman, M. A. & Banerjee, A. K. *J. Virol.,* 71, 4272-4277 (1997).
Honda, A., K. Ueda, K. Nagata, and A, Ishihama., *J. Biochem.* (Tokyo), 104, 1021-1026 (1988).
Horimoto, T. & Kawaoka, Y. *J. Virol.,* 68, 3120-3128 (1994).
Huddleston, J. A. & Brownless, G. G. *Nucl. Acids Res.,* 10, 1029-1037 (1982).
Jin, H., G. P. Leser and R. A. Lamb. *EMBO J.,* 13, 5504-5515 (1994).
Jin, H., G. P. Leser, J. Zhang, and R. A. Lamb. *EMBO J.,* 16, 1236-1247 (1997).
Kato, A., Sakai, Y., Shioda, T., Kondo, T., Nakanishi, M. & Nagai, Y. *Genes Cells,* 1, 569-579 (1996).
Keitel, W. A. & Piedra, P. A. in *Textbook of Influenza*, eds. Nickolson, K. G., Webster, R. G., and Hay, A. (Blackwell, Oxford), pp. 373-390 (1998).
Kovesdi, I., Brough, D. E., Bruder, J. T. & Wickham, T. J. *Curr. Opin. Biotechnol.,* 8, 583-589 (1997).
Lasko et al. *Proc. Natl. Acad. Sci. USA,* 89, 6232 (1992).
Lawson, N. D., Stillman, E. A., Whitt, M. A. & Rose, J. K. *Proc. Natl. Acad. Sci. U.S.A.,* 92, 4477-4481 (1995).
Leahy, M. B., Dessens, J. T., and Nuttall, P. A. *J. Virol.,* 71, 8347-8351 (1997).
Leahy, M. B., Dessens, J. T., and Nuttall, P. A. *J. Virol.,* 71, 8352-8356 (1997).
Leahy, M. B., Dessens, J. T., Pritlove, D. C., and Nuttall, P. A. *J. Virol.,* 72, 2305-2309 (1998).
Li, S., Xu, M. & Coelingh, K. *Virus Res.,* 37, 153-161 (1995).
Luytjes, W., Krystal, M., Enami, M., Parvin, J. D. & Palese, P. *Cell,* 59, 1107-1113 (1989).
Mena, I., Vivo, A., Pérez, E. & Portela, A. *J. Virol.,* 70, 5016-5024 (1996).
Naim, H. Y. and M. G. Roth. *J. Virol.,* 67, 4831-4841 (1993).
Neumann, G., Castrucci, M. R. & Kawaoka, Y. *J. Virol.,* 71, 9690-9700 (1997).
Neumann, G., Zobel, A. & Hobom, G. *Virology,* 202, 477-479 (1994).
Niwa, H., Yamamura, K. & Miyazaki, J. *Gene,* 108, 193-200 (1991).
Palese, P., Zheng, H., Engelhardt, 0. G., Pleschka, S. & Garcia-Sastre, A. *Proc. Natl. Acad. Sci. U.S.A.,* 93, 11354-11358 (1996).
Perez, D. R. & Donis, R. O. *Virology,* 249, 52-61 (1998).
Pichel et al. *Oncogene,* 8, 3333 (1993).
Pleschka, S., Jaskunas, S. R., Engelhardt, O. G., Zürcher, T., Palese, P. & Garcí a-Sastre, A. *J. Virol.,* 70, 4188-4192 (1996).
Radecke, F., Spielhofer, P., Schneider, H., Kaelin, K., Huber, M., Dotsch, C., Christiansen, G. & Gilleter, M. A. *EMBO J.,* 14, 5773-5784 (1995).
Schnell, M. J., Mebatsion, T., and Conzelmann, K. K. *EMBO J.,* 13, 4195-4203 (1994).
Struhl, K. *NAR,* 13, 8587 (1985).
Struhl, K. et al. *J. Mol. Biol.,* 152, 553 (1985).
Subbarao, E. K., Kawaoka, Y. & Murphy, B. R. *J. Virol.,* 67, 7223-7228 (1993).
Weber, F., Haller, O., and Kochs, G. *J. Virol.,* 70, 8361-8367 (1996).
Weber, F., Haller, O., and Kochs, G. *Arch. Virol.,* 142, 1029-1033 (1997).
Whelan, S. P., Ball, L. A., Barr, J. N. & Wertz, G. T. *Proc. Natl. Acad. Sci. U.S.A.,* 92, 8388-8392 (1995).

Yasuda, J., Bucher, D. J. & Ishihama, A. *J. Virol.*, 68, 8141-8146 (1994).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for producing reassortant influenza virus particles for preparation of a vaccine, comprising:

i) introducing a first set of expression vectors into cells containing a nucleoprotein and an RNA dependent RNA polymerase, wherein said vectors comprise genomic influenza vRNA segments or antigenomic cRNA segments of said genomic influenza vRNA segments;

ii) culturing said cells in the absence of helper virus such that ribonucleoprotein complexes containing the genomic influenza vRNA segments are formed and reassortant influenza viral particles comprising the genomic influenza vRNA segments is assembled in said cells; and iii) recovering said reassortant influenza viral particles from said cells.

2. The method of claim 1, wherein the cells are from a cell line comprising a second set of vectors encoding said nucleoprotein and the subunits of said RNA-dependent RNA polymerase.

3. The method of claim 1, wherein said virus is an influenza virus of type A, B or C.

4. The method of claim 1, wherein said reassortant influenza virus contains vRNA segments derived from more than one parent virus.

5. The method of claim 1, wherein the culturing step occurs in an egg.

6. The method of claim 1, further comprising attenuating the recovered reassortant influenza viral particles.

7. The method of claim 1, wherein the first and second set of vectors are introduced by liposomal transfection.

8. The method of claim 1, wherein the first and second set of vectors are all plasmids.

9. The method of claim 1, wherein each of said genomic influenza vRNA segments or antignomic cRNA segments of said genomic influenza vRNA segments are encoded on separate vectors.

10. The method of claim 1, wherein the RNA polymerase I promoter is a human RNA polymerase I promoter.

11. The method of claim 1, wherein a coding sequence for each genomic influenza vRNA segments or antigenomic cRNA segments of said genomic influenza vRNA segments is upstream of a transcription terminator.

* * * * *